(12) United States Patent
Kadota et al.

(10) Patent No.: US 11,274,054 B2
(45) Date of Patent: Mar. 15, 2022

(54) SYNTROPHIC ENRICHMENT FOR ENHANCED DIGESTION PROCESS

(71) Applicants: Metro Vancouver Regional District, Burnaby (CA); Greater Vancouver Sewerage & Drainage District, Burnaby (CA)

(72) Inventors: Paul Kadota, Port Coquitlam (CA); Paul Markin, Kelowna (CA); Cigdem Eskicioglu, Kelowna (CA)

(73) Assignees: METRO VANCOUVER REGIONAL DISTRICT, Burnaby (CA); GREATER VANCOUVER SEWERAGE & DRAINAGE DISTRICT, Burnaby (CA)

( * ) Notice: Subject to any disclaimer, the term of this patent is extended or adjusted under 35 U.S.C. 154(b) by 0 days.

(21) Appl. No.: 16/895,434

(22) Filed: Jun. 8, 2020

(65) Prior Publication Data
US 2020/0392025 A1 Dec. 17, 2020

Related U.S. Application Data

(60) Provisional application No. 62/859,844, filed on Jun. 11, 2019.

(51) Int. Cl.
*C02F 3/28* (2006.01)
*C12P 5/02* (2006.01)
(Continued)

(52) U.S. Cl.
CPC .......... *C02F 3/2826* (2013.01); *C02F 3/2806* (2013.01); *C02F 3/2873* (2013.01);
(Continued)

(58) Field of Classification Search
CPC .......... C02F 3/2826; C02F 9/00; C02F 11/04; C02F 3/2806; C02F 3/2893; C02F 3/2873;
(Continued)

(56) References Cited

U.S. PATENT DOCUMENTS 6,783,677 B1 * 8/2004 Irani .................. C12M 25/00
210/603
8,404,111 B2 3/2013 Bae et al.
(Continued)

FOREIGN PATENT DOCUMENTS

CN 102557250 A 7/2012
CN 104556369 A 4/2015
(Continued)

OTHER PUBLICATIONS

Zhao et al, "Potentially shifting from interspecies hydrogen transfer to direct interspecies electron transfer for syntrophic metabolism to resist acidic impact with conductive carbon cloth", Chemical Engineering Journal, vol. 313, pp. 10-18, (2017).
(Continued)

*Primary Examiner* — Fred Prince
(74) *Attorney, Agent, or Firm* — DLA Piper LLP US

(57) ABSTRACT

A syntrophic enrichment for enhanced digestion (SEED) system is presented, in which a retrofit addition to existing anaerobic digestion infrastructure provides improved digestion process rate and biogas quality. The system provides optimal niche environments for accelerating fermentative, syntrophic and methanogenic metabolisms to increase digestion system loading rates and enhance main digester microbiome. Prescribed media formulations, reactor integrations, and operational methods using various fixed and loose media enhance global digestion system performance.

(Continued)

The retrofitted system enables existing plants to transition from an outdated solids-management model to one of valorized biomethane production.

22 Claims, 15 Drawing Sheets

(51) Int. Cl.
    *C02F 11/04*     (2006.01)
    *C02F 9/00*     (2006.01)
    *C12M 1/12*     (2006.01)
    *C12M 1/00*     (2006.01)
    *C12M 1/08*     (2006.01)
    *C02F 101/30*     (2006.01)
    *C12M 1/107*     (2006.01)

(52) U.S. Cl.
    CPC .............. *C02F 3/2893* (2013.01); *C02F 9/00* (2013.01); *C02F 11/04* (2013.01); *C12M 23/06* (2013.01); *C12M 23/28* (2013.01); *C12M 25/00* (2013.01); *C12M 25/02* (2013.01); *C12M 27/24* (2013.01); *C12M 29/04* (2013.01); *C12M 29/08* (2013.01); *C12P 5/023* (2013.01); *C02F 2101/30* (2013.01); *C02F 2203/006* (2013.01); *C02F 2301/046* (2013.01); *C12M 21/04* (2013.01); *Y02E 50/30* (2013.01)

(58) Field of Classification Search
    CPC ............ C02F 2301/046; C02F 2101/30; C02F 2203/006; C12M 25/02; C12M 29/08; C12M 27/24; C12M 23/06; C12M 25/00; C12M 23/28; C12M 29/04; C12M 21/04; C12P 5/023; Y02E 50/30
    USPC .......................... 210/603, 615, 616, 617, 259
    See application file for complete search history.

(56) References Cited

U.S. PATENT DOCUMENTS

2010/0304420 A1* 12/2010 Gray ...................... C12M 21/04
                                                                                                                                                     435/29
2012/0118808 A1     5/2012  Bae et al.

FOREIGN PATENT DOCUMENTS

WO       2011111879 A1     9/2011
WO       2017174093 A2    10/2017

OTHER PUBLICATIONS

PCT International Application No. PCT/IB2020/000446, Written Opinion of the International Searching Authority, dated Nov. 10, 2020, 6 pages.

PCT International Application No. PCT/IB2020/000446, International Search Report of the International Searching Authority, dated Nov. 10, 2020, 4 pages.

King et al, "The Future of Industrial Biorefineries", World Economics Forum, Geneva, (2010).

Cimon et al, "Effect of biochar and wood ash amendment on biochemical methane production of wastewater sludge from a temperature phase anaerobic digestion process", Bioresource Technology, vol. 297, pp. 1-10, Nov. 18, 2019.

Zhao et al, "Towards engineering application: Potential mechanism for enhancing anaerobic digestion of complex organic waste with different types of conductive materials", Water Research, vol. 115, pp. 266-277, Mar. 1, 2017.

* cited by examiner

SYNTROPHIC ENRICHMENT FOR ENHANCED DIGESTION PROCESS

PRIORITY

The present application claims the benefit of U.S. Provisional Application No. 62/859,844, filed on Jun. 11, 2019, which is incorporated by reference in its entirety herein.

FIELD

The disclosure relates to treatment of wastewater solids and gas, whereby sludge separated from the wastewater is converted to biogas or renewable natural gas by way of high-rate electroactive biochemical metabolisms and adsorptive chemistry.

BACKGROUND

Closing the carbon cycle on industrial scales is becoming an imperative for the building of long-term sustainable societies. The organic matters present in municipal, industrial, agricultural and other sources of wastewater represent a largely under-utilized resource for energy and value-added products. If harvested, these under-utilized resources will help interconnect the circular economy, an alternative to traditional linear economy (make, use, dispose) in which we keep resources in use for as long as possible, extract the maximum value from them whilst in use, then recover and regenerate products and materials at the end of each service life. In 2012, the Water Environment Foundation (WEF) changed its standard terminology from wastewater treatment plant to water resource recovery facility (WRRF) in order to focus on the products and benefits of treatment rather than the waste coming into facilities. By focusing on end products such as biofuels, bio-energy, and manufacturing precursor chemicals, WRRFs may acquire the tools and technology to become carbon neutral and energy positive "biorefineries." The World Economic Forum defines biorefineries as "a facility that integrates biomass conversion processes and equipment to produce fuels, chemicals, feed, materials and energy from biomass." (King, et al., (2010), The Future of Industrial Biorefineries. World Economics Forum, Geneva) The realization of WRRFs as biorefineries requires a suite of technologies designed to exploit specific microbiological consortia containing desirous metabolic pathways, rather than relying on the de-facto metabolisms of spontaneous local assemblages.

SUMMARY

Disclosed herein is a bioreactor in an anaerobic digestion system for treating wastewater. In some embodiments, the bioreactor can include an enclosed cylinder, which can include a central draft tube, a main annular space surrounding the central draft tube, an electroactive medium dispersed within the enclosed cylinder, an inlet for introducing a feedstock into the enclosed cylinder in contact with the electroactive medium, and an outlet for outputting the feedstock after treatment. In some embodiment, the feedstock can be sludge and/or wastewater. In some embodiments, the electroactive medium can be in a fixed configuration. In some embodiments, the electroactive medium can include a basal cloth support sandwiched by two layers of carbon cloth. A steel, polyethylene or polycarbonate screen can be placed on the carbon cloth to provide a turbulent flow for an enhanced mass transfer and longevity. A conductive nanomaterial can be bonded onto the carbon cloth.

In some embodiments, the electroactive medium can be configured into a pleated, a lobate arrangement, a honeycomb arrangement, a flat pack cartridge, or a spiral wrap arrangement. In some embodiments, a filter device including the electroactive medium can be placed in the main annular space. The electroactive medium can be loose, which can be selected from biochar, activated carbon, wood ash, and magnetic mineral. In some embodiments, the electroactive medium can be natural or man-made. The loose electroactive medium can be dispersed throughout the central draft tube and the main annular space. In some embodiments, the loose electroactive medium can be contained within a porous receptacle.

In some embodiments, the bioreactor can include a replaceable container to contain the loose electroactive medium in a second annular space defined by the central draft tube and the container. The replaceable container can include an outer barrier wrap to allow the feedstock to flow between the main annular space and the second annular space but contain the loose electroactive medium inside the container.

Also disclosed herein is an anaerobic digestion system for treating wastewater. In some embodiments, the system can include the bioreactor as well as a main anaerobic digester placed downstream of the bioreactor. In some embodiments, the system can also include a fermentation section placed upstream of the bioreactor. In some embodiments, the fermentation section and the bioreactor can be integrated into one reactor vessel. The electroactive medium can be loose and magnetic. In some embodiments, a recycler can be used downstream of the bioreactor and/or the main anaerobic digester to collect the magnetic loose electroactive medium. Electromagnets can be used in the magnetic media recycler to gather magnetic loose media from bioreactor and/or main anaerobic digester discharge sludge, and recycle both the magnetic loose media and its associated biomass upstream for long-term retention within the anaerobic digestion system.

Further disclosed herein is a method of treating wastewater using an anaerobic digestion system. In some embodiments, the method can include introducing a feedstock including a sufficient concentration of low molecular weight organics derived from the wastewater into a bioreactor, circulating the feedstock in contact with an electroactive medium dispersed inside the bioreactor, growing a biofilm from the feedstock, a methanogen, and a syntrophic bacterium on the electroactive medium, and converting the low molecular weight organics into a biogas within the anaerobic digestion system, thereby increasing a methane content in the biogas and increasing the digestion system capacity. In some embodiments, the method can include back injecting a fraction of the biogas or an externally-generated hydrogen into the bioreactor for mixing, purification, or amelioration of methane production. The method can also include scouring the biofilm from the electroactive medium by a liquid shear force of the feedstock and/or the biogas injection. In some embodiments, the method can include dosing a biocatalyst including the biofilm and an electron-conductive supplement into a main anaerobic digester downstream of the bioreactor. In some embodiments, the method can also include collecting the biogas from the bioreactor and/or the main anaerobic digester. In some embodiments, the electroactive medium can include a loose electroactive medium.

BRIEF DESCRIPTION OF THE DRAWINGS

In order to facilitate a full understanding of the present disclosure, reference is now made to the accompanying drawings, in which like elements are referenced with like numerals. These drawings should not be construed as limiting the present disclosure, but are intended to be illustrative only. The drawings are not necessarily to scale, or inclusive of all elements of a system, emphasis instead generally being placed upon illustrating the concepts, structures, and techniques sought to be protected herein.

DESCRIPTION

Figure 1:
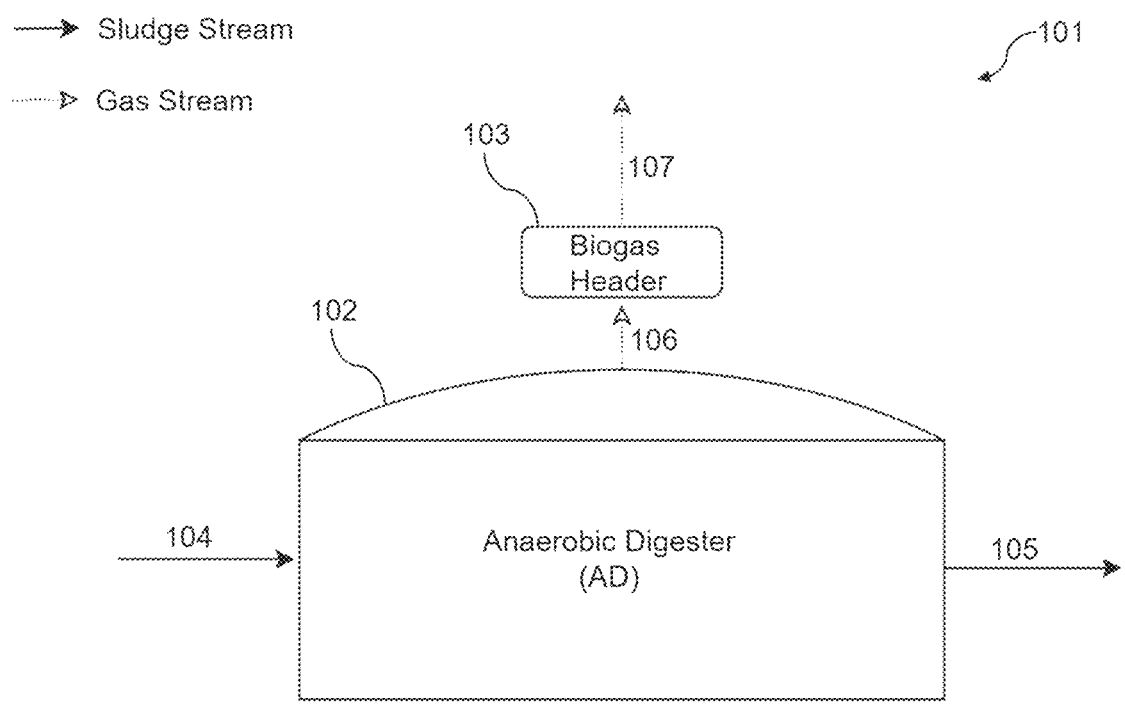
FIG. 1 is a schematic of a configuration of a conventional anaerobic digestion system.

Disclosed herein are embodiments of a device and method for treating wastewater in order to increase anaerobic treatment rate and obtain improved biogas from an anaerobic digestion system. A bioreactor is disclosed which can be configured as a retrofit chamber to a state-of-the-art anaerobic digestion system. The reactor and anaerobic digestion system in the present disclosure can facilitate the conversion of organic matter into methane through a series of microbial mediated biotransformations including hydrolysis, fermentation (acidogenesis and alcohol production), acetogenesis, syntrophy and methanogenesis. Direct interspecies electron transfer (DIET) is a microbial syntrophy where cell-to-cell electron transfer occurs between syntrophic microbial species. DIET between bacteria and methanogenic archaea in anaerobic digestion can accelerate the syntrophic conversion of various reduced organic compounds to methane. A fermentation section can be used upstream of the disclosed bioreactor to pre-treat the wastewater sludge. In some embodiments, the fermentation process can be conducted in a separate reaction vessel. In some embodiments, the fermentation section can be integrated in the same vessel as the bioreactor process. In some embodiments, a synthetic bioreactor feed is used, which is already rich in desirable reduced organic compounds, and precludes the need for an upstream sludge fermentation process. The bioreactor in the present disclosure can include an enclosed cylinder, which can include a central draft tube, a main annular space surrounding the central draft tube, an electroactive medium dispersed within the enclosed cylinder, an inlet for introducing a feedstock into the enclosed cylinder in contact with the electroactive medium, and an outlet for outputting the feedstock after treatment. The disclosed bioreactor can generate biofilm and enable a DIET pathway in the anaerobic digestion system, resulting in a higher metabolic rate and better biogas quality, thereby increasing the digestion system capacity.

The electroactive media used for the disclosed bioreactor can be natural or man-made. The electroactive media can be in a fixed configuration or loose. The fixed electroactive media can include, but are not limited to, biochar, activated carbon, wood ash, carbon cloth, and magnetic material. In some embodiments, loose electroactive media such as biochar, activated carbon, wood ash, magnetic material, and mixture thereof can be affixed and/or impregnated on a fixed medium such as a common fabric cloth, which can transform these loose electroactive media into a fixed configuration. The electroactive media in a fixed configuration can include, but is not limited to, a pleated arrangement, a lobate arrangement, a honeycomb arrangement, a flat pack cartridge, a spiral wrap arrangement, which may or may not be extruded. In some embodiments, the electroactive media in a fixed configuration can include a basal cloth support sandwiched by two layers of carbon cloth. A steel, polyethylene, or polycarbonate screen can be placed on the carbon cloth to provide a turbulent flow for an enhanced mass transfer and longevity. The loose electroactive media can include, but are not limited to, biochar, activated carbon, wood ash, and magnetic mineral. The loose electroactive media can be dispersed throughout the central draft tube, the main annular space, and/or contained within a porous receptacle. In some embodiments, "loose medium" or "loose media" can include, but is not limited to, granular, particulate, powder and any other physical appearance that is non-bonded, unattached, moving, or free. The electroactive media can promote methanogenesis reactions for accelerated growth and enriched microbial consortia and/or successional changes in a microbial community to increase biomethane production.

The important bioreactor design and operational parameters that can be optimized for an ultimate anaerobic degradation enhancement can include, but are not limited to, media type, media particle size, media dosage to bioreactor, and organic loading rate of bioreactor. As media particle size decreases, the surface area per unit volume (or mass) increases. The ideal media can provide high surface area for biofilm formation and adsorption of inhibitory compounds (including, but are not limited to, ammonium, heavy metals and volatile fatty acids) and pH buffering capacity. The media can also be non-biodegradable (durable/stable) in the bioreactor. As an additional advantage, carbonaceous material, such as granular and powdered activated carbon, carbon cloth, graphene and graphite can be good candidates for electron flow because they are electrically conductive, which can promote microbial diversity. Every material has its own advantages/disadvantages and the syntrophy among cultures can be governed by more than one factor; therefore mixing various loose media can have potential to present unique advantages over the use of single medium.

The instant disclosure can be a side-stream or up-stream bioreactor with the purpose of enhancing populations of desired microbial cultures within it, and adding the enhanced culture to the anaerobic digestion system. The environment of the disclosed bioreactor is designed to meet syntrophic bacteria and methanogens' preferred growth conditions. In some embodiments, the proposed bioreactor can increase the methane content of biogas produced by the full-scale anaerobic digestion by functioning as a non-invasive retrofit. The existing digestion equipment such as fermentation and main digester vessels in the anaerobic digestion system can be used without major modifications. The disclosed bioreactor can be added as an additional element in the state-of-the-art digestion system and conveniently improve the biogas quality generated therefrom. The bioreactor can receive synthetic or actual wastewater feed rich in low molecular weight substrate, i.e., the products of acidogenesis, acetogenesis, and optionally hydrolysis, and can use this feed to increase the abundance and activity of methanogenic archaea and syntrophic bacteria, and in the next step can optionally dose this enriched biofilm sludge as a biocatalyst into the main digester. Tchobanoglous et al. (2014) Metcalf & Eddy Inc., Wastewater Engineering: Treatment and Resource Recovery, 5th ed. McGraw-Hill Education, New York. Greater abundance and activity of these key digester populations within the main digester can relieve biological constraints on the methanogenesis pathway and result in greater methane production rate as well as content in the resultant biogas.

As used herein, anaerobic digestion can refer to a complex biochemical process of biologically mediated reactions by a consortium of microorganisms to convert organic compounds into a biogas including methane and carbon dioxide. An anaerobic digestion process can include four stages, (1) hydrolysis, (2) acidogenesis, (3) acetogenesis, and (4) methanogenesis. Hydrolysis, acidogenesis, and acetogenesis can refer to biological and/or chemical reactions where particulates are solubilized and large polymers converted into low molecular weight organics (LMWO) including, but not limited to, volatile fatty acids (VFAs), simple alcohols (methanol, ethanol, etc.), and acetates. Methanogenesis can refer to biological reactions where acetates are disproportionated into methane and carbon dioxide, or where molecular hydrogen and carbon dioxide are converted to methane and water. Other types of methanogenesis include methylotrophic methanogenesis, where compounds such as methanethiol or methylamine are converted to methane. Another type of methanogenesis can be direct interspecies electron transfer (DIET) methanogenesis, where reducing equivalents are obtained not from mediating soluble chemicals but through direct partnerships with bacteria.

As used herein, biofilm can refer to a syntrophic consortium of aggregated microorganisms in which cells that are frequently embedded within a self-produced matrix of extracellular polymeric substances (EPSs) adhere to each other and/or to a surface. As used herein, biocatalyst can refer to harvested biofilm content from electroactive media inside the disclosed bioreactor, optionally with the addition of an electron-conductive supplement.

As used herein archaea can refer to a domain of single-celled microorganisms, which can exhibit unique properties separating them from bacteria and eukarya. As used herein, chemical oxygen demand (COD) is a measure of the capacity of water to consume oxygen during the decomposition of organic matter and the oxidation of inorganic chemicals such as Ammonia and nitrite. COD measurements are commonly made on samples of wastewater or natural waters contaminated by domestic or industrial wastes. As used herein, bioaugmentation can refer to a process to facilitate a methanogenesis pathway in an anaerobic digestion process, which can result in faster methane production and/or higher biomethane content in the generated biogas. A used herein, bioaugmentor can refer to a device or instrument to perform the bioaugmentation process. A pilus or its plural form pili can refer to a hair-like appendage found on the surface of many bacteria.

Anaerobic digestion can be performed as a batch process or a continuous-flow process. In a batch system, biomass is added to the reactor at the start of the process. The reactor is then sealed for the duration of the process until digestion of the organic matter has completed. Using more than one batch reactor at a plant can ensure constant production of biogas. In continuous digestion processes, organic matter is constantly added or added in stages to the reactor. In continuous digestion, the end products can be constantly or periodically removed, resulting in constant production of biogas.

The wastewater treatment process can be divided into liquid stream treatment and solid stream treatment. In liquid stream treatment, suspended particulates can be settled as primary sludge, and dissolved nutrients can be consumed by aerobic bacteria which are removed as secondary sludge and the resulting effluent is discharged to the environment, in accordance with regulations. In solid stream treatment, primary and secondary sludge can be treated in anaerobic digesters by microbial communities consisting mostly of bacteria (hydrolyzers, fermenters, syntrophs) and some archaea (methanogens).

Sludge processing represents one of the major challenges at water resource recovery facilities (WRRFs), often costing more than the treatment and discharge of the liquid stream. Among several treatment options for waste sludge treatment, anaerobic digestion has proven to be an effective technology. One aspect of anaerobic digestion that can be improved is the current slow process rates which result in long sludge retention times (time that the sludge solids are in the system), as well as low biogas methane content.

Anaerobic digestion is a collection of processes by which microorganisms break down biodegradable material in the absence of oxygen. FIG. 1 is a schematic of a configuration of a conventional anaerobic digestion system 101 with a main anaerobic digester (AD) 102, and a biogas header 103. The biogas header can be a primary pipeline in a biogas production and/or storage facility that transports biogas from the production vessel and/or storage caverns to and from each interconnecting pipeline. In this figure, the solid line arrows indicate the flow of a sludge stream, while the dotted line open arrows indicate the flow of a gas stream. A sludge feed 104 can be injected into the anaerobic digestion system, which can be first processed by AD 102. A digestate 105 can be released from AD 102 to a drain. A biogas stream 106 can be generated from AD 102 and collected by biogas header 103. An output biogas stream 107 can be used for downstream applications.

Anaerobic digestion is widely used as a source of renewable energy. The output biogas stream 107 can consist of methane, carbon dioxide and traces of other contaminant gases. This biogas can be used directly as fuel, in combined heat and power gas engines or upgraded to natural gas-quality biomethane.

As discussed above, the anaerobic digestion process can include the following biological reactions: hydrolysis, fermentation (acidogenesis and alcohol production), acetogenesis and methanogenesis that are mediated by diverse microbial communities through interconnected metabolic processes. There can be different configurations for a conventional AD system. In a single-stage digestion system, all of the biological reactions can occur within a single sealed reactor. In a two-stage digestion system, and depending on hydraulic retention times, a majority of the first three biological reactions (hydrolysis, acidogenesis, and acetogenesis) can be performed in the first stage and methanogenesis can be performed in a separate digestion vessel.

The digestion process can begin with bacterial hydrolysis of sludge. Insoluble organic polymers, such as carbohydrates, are broken down to soluble derivatives (simple monomers such as glucose and amino acids) that become available for other bacteria. Acidogenic bacteria (i.e., fermenters) can then convert the glucose and amino acids into carbon dioxide, hydrogen, ammonia, and volatile fatty acids. Concurrently and subsequently, acetogenic organisms can convert carbon dioxide and an electron source (e.g., hydrogen, formate, carbon monoxide) into acetic acid. All these products are included in a sludge feed 104 and delivered into AD 102 for methanogenesis. Inside AD 102, methanogens convert the sludge feed to biogas stream 106 and digestate 105. Biogas stream 106 is mostly composed of carbon dioxide and methane, with trace amounts of hydrogen sulphide and other gases. Methane is a valuable component of biogas, and is produced by a partnership between methanogenic archaea and syntrophic bacteria. Modification of the anaerobic digestion microbiome composition and activity can increase the methane production rate by up to 25%, while adsorptive capacities of media, in addition to the autotrophic methanogenic metabolisms, can increase biogas content beyond the status-quo of 50-60%.

TABLE 1

Exemplary mechanisms of the four types of methanogenesis pathways

| Pathways | Reaction Equation |
|---|---|
| Hydrogenotrophic Methanogenesis | $4H_2 + CO_2 \rightarrow CH_4 + 2H_2O$ |
| Acetoclastic Methanogenesis | $CH_3COO^- + H^+ \rightarrow CH_4 + CO_2$ |
| Methylotrophic pathway (amine) | $4CH_3NH_2 + 2H_2O \rightarrow 3CH_4 + CO_2 + 4NH_3$ |
| DIET pathway | $9H^+ + 8e^- + HCO_3^- \rightarrow CH_4 + 3H_2O$ |

An important group of microbial species involved in the process of anaerobic digestion are methanogenic archaea (methanogens), which can be performed in AD 102. Some methanogens can metabolize acetate directly and produce methane as a byproduct, a metabolic pathway called aceticlastic methanogenesis, which per reaction yields −31 kJ/mol for cell maintenance and proliferation. Some methanogenic species can combine $H_2$ as an electron donor with $CO_2$ to produce methane, a metabolic pathway called hydrogenotrophic methanogenesis, which yields −136 kJ/mol for cell growth and proliferation, which is substantially more than acetoclastic metabolism. The mechanisms of these two methanogenesis pathways are shown in Table 1 above. In aceticlastic methanogenesis, for each molecule of acetate consumed, equal amounts of carbon dioxide and methane are produced. In hydrogenotrophic methanogenesis, for every four molecules of hydrogen gas consumed, one molecule of carbon dioxide is also consumed to produce methane and two molecules of water. Thus, while aceticlastic methanogenesis produces carbon dioxide, the hydrogenotrophic methanogenesis process can effect a net decrease in carbon dioxide.

Under normal conditions, hydrogenotrophic methanogenesis contributes roughly one-third of the methane produced through the metabolism of acetate and other suitable compounds. Increasing the availability of molecular hydrogen in the anaerobic digester would thus favor hydrogenotrophs over acetoclasts and reduce relative amounts of $CO_2$ as a byproduct in the biogas. However, high partial pressures of molecular hydrogen can inhibit bacteria which produce molecular hydrogen as a byproduct of VFA oxidation, and therefore this practice can destabilize digestion. Alternatively, enabling microbes to reduce $CO_2$ and hydrogen ions to methane by providing them with electrons can similarly favor methane formation, but without any destabilizing effects.

In some embodiments, the anaerobic digestion system in the present disclosure relies on direct interspecies electron transfer (DIET), which can accelerate the syntrophic conversion of various reduced organic compounds to methane. DIET-based syntrophy can naturally occur in some anaerobic digesters via biologically produced conductive pili and outer membrane cytochromes, however, it can be engineered via different methods such as the addition of various non-biological conductive materials to enhance the anaerobic digester performance, or by stimulation of the microbiome to increase expression of genes coding for DIET enabling exopolymers and electron shuttles.

Figure 2:
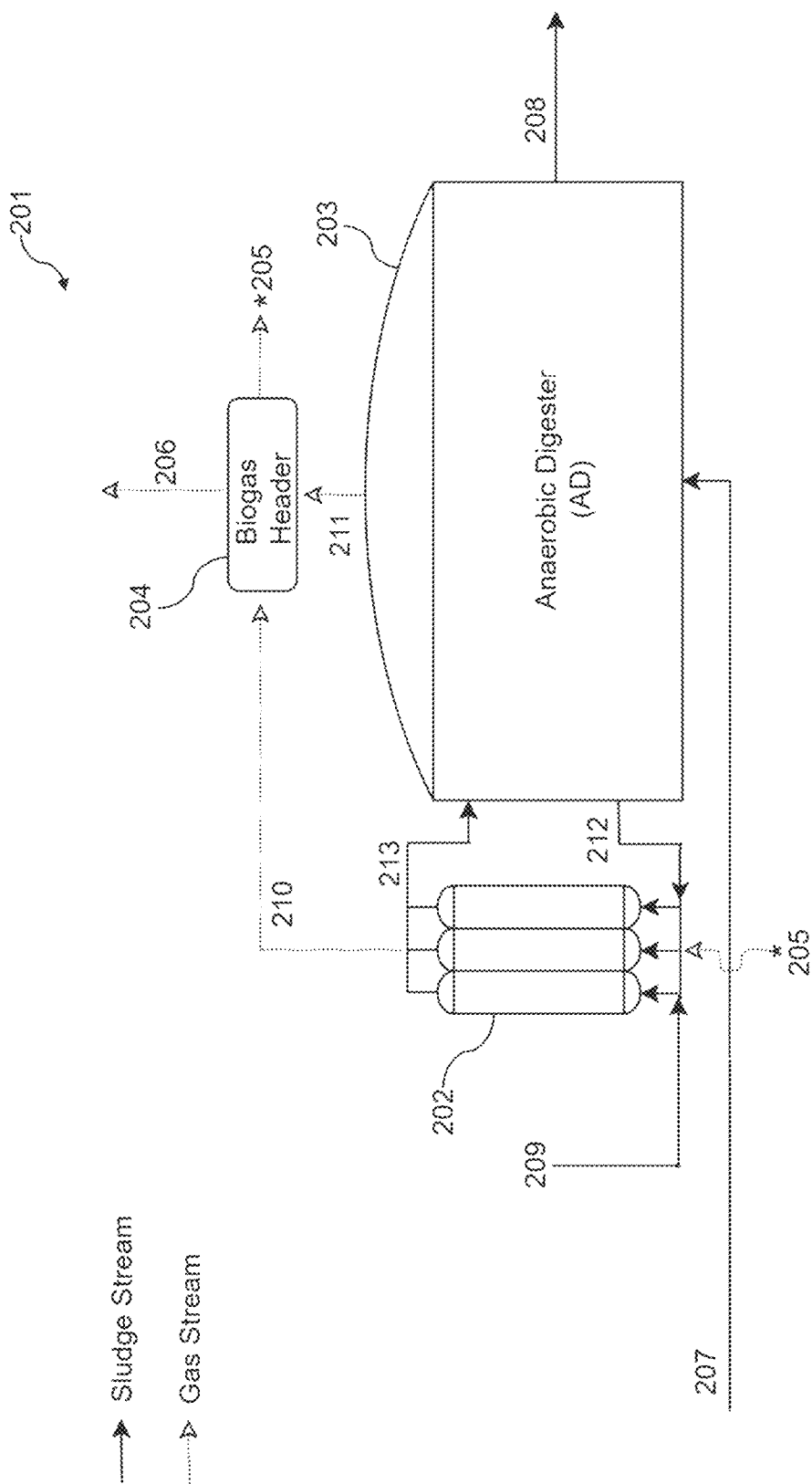
FIG. 2 is a schematic of a configuration of an anaerobic digestion system having a bioreactor, according to some embodiments of the present disclosure.

FIG. 2 is a configuration of an anaerobic digestion system 201 with a bioreactor 202, according to some embodiments of the present disclosure. The solid line arrows indicate flow of a sludge stream, while the dotted line open arrows indicate flow of a gas stream. A recycle loop of sludge flow is formed between the bioreactor and the main digester. The configuration shown by FIG. 2 aims at providing optimal feed substrates to the bioreactor, thereby creating a synergistic system between the bioreactor and AD, and generating a high-quality biogas product in-situ from the bioreactor. The biogas is collected from a biogas header 204. Anaerobic digestion system 201 can include bioreactor 202, an AD 203, and biogas header 204. An AD feed 207 can be injected into AD 203. An AD sludge 212 can be injected into bioreactor 202 for inoculation of scoured or fresh media, and after treatment released as a bioreactor sludge 213 back into AD 203. A bioreactor feed 209 can be injected into bioreactor 202 to facilitate rapid growth of high-rate methanogenic biofilms on the inoculated media. A digestate 208 after treatment can be released from AD 203. A bioreactor biogas stream 210 can be generated from bioreactor 202 and collected by biogas header 204. Biogas header 204 can also collect AD biogas stream 211 produced by AD 203. Up to 100% of the biogas generated from AD 203 and bioreactor 202 can form a reused biogas stream 205 and be back injected into the bottom of bioreactor 202 for removal of carbon dioxide, mixing, and backwashing. In some embodiments, an externally-generated hydrogen can also be used for back injection. Alternatively, waste carbon dioxide gas from downstream biogas upgrading equipment (not shown) can be injected into the bottom of bioreactor 202 for removal within the bioreactor, conversion to methane, mixing, and backwashing. A final output biogas stream 206 can be collected for downstream applications. Such a configuration focuses on injecting optimal LMWO substrates to bioreactor 202 in order to maximally enrich for DIET consortia within the bioreactor and downstream AD. Such a configuration of anaerobic digestion system can be used to maximize chemical oxygen demand (COD) attenuation of the AD feed sludge, thereby increasing AD capacity.

The disclosed bioreactor herein contains electroactive media (discussed below in FIGS. 3-6) for the enrichment of a high-rate microbial consortium in a side-stream or up-stream (pre-treatment) configuration relative to the main anaerobic digester (AD). The disclosed bioreactor, when considered together with the AD, can constitute the anaerobic digestion system for the treatment of wastewater. In some embodiments, a prior fermentation process (not shown) can optionally be performed upstream of the bioreactor. Use of the disclosed bioreactor can improve anaerobic digestion system performance, whether strictly in the bioreactor themselves or downstream in the AD, by way of the following four functions: methane production rate, methane content in biogas, COD removal rate, and process stability. The disclosed bioreactor can be a bolt-on retrofit chamber, or array of chambers, to existing conventional anaerobic digestion infrastructure, and may include a pre-fermentation step for the sludge feed to condition it prior to contact with the electroactive media in the bioreactor.

Sludge stream in anaerobic digestion system 201 can include AD feed 207, bioreactor feed 209, AD sludge 212 to bioreactor 202, bioreactor sludge 213 back into AD 203, and digestate 208 to a downstream process, such as mechanical dewatering and cake formation. AD sludge 212 and bioreactor sludge 213 can form an inoculating recycle loop passing through bioreactor 202, which can ensure methanogens are pre-adapted to the AD environment. In some embodiments, bioreactor sludge 213 can include biofilm components including cells and extracellular polymeric substances (EPS) from ripened electroactive media from bioreactor 202. During regular biofilm growth, bioreactor feed 209 to bioreactor 202 can be active, while AD sludge 212 to bioreactor 202 is shut down. This can ensure the sludge feed injected into bioreactor 202 contains an optimal composition with sufficient concentration of LMWOs, which can enable an effective biofilm growth inside the bioreactor. After the biofilm growth, scour and harvest is finished, bioreactor feed 209 can be shut down, and AD sludge 212 can be active, which can facilitate bioreactor re-inoculation. Bioreactor feed 209 can be a synthetic wastewater mixture including but not limited to LMWO ingredients such as ethanol and/or acetate. Trace mineral salts helpful for methanogen growth can also be added to synthetic wastewater mixtures, including salts containing cobalt, nickel, molybdenum, tungsten, zinc and iron, as well as other nutrient salts such as ammonium chloride, sodium chloride, magnesium chloride, calcium chloride, dipotassium phosphate, sodium sulphate and sodium bicarbonate. Alternatively, bioreactor feed 209 can instead be derived from labile sludges such as primary municipal sludge (PS) or thickened screened primary municipal sludge (TSPS). PS or TSPS streams can be enhanced by extending their retention time in holding tanks, flow-through vessels, or thickening basins from hours to up to five days in order to facilitate fermentative generation of LMWO. PS or TSPS, whether fermented or not, may also receive trace mineral and nutrient salts as indicated above in order to create bioreactor feed 209. In some embodiments, bioreactor feed 209 may be composed of either a fraction of, or all of, AD feed 207, providing sufficient LMWO substrate concentrations are present in AD feed 207. AD feed 207 may be composed of primary sludge, waste secondary sludge, mixed sludges composed of a mixture of primary and secondary sludge, or fermented versions of primary, waste secondary, or mixed sludges. Sludge temperature control equipment, which is not depicted in FIG. 2, can be used to modify or maintain the temperature of AD feed 207 at a desired value before injection into AD 203, and the temperature of bioreactor feed 209 at a desired value before injection into bioreactor 202. The temperature control equipment can involve an external heat exchange manifold, which transfers heat from water to sludge or vice-versa by means of counter-current isolated flow. If sludges of two differing temperatures are required in the digestion system, a sludge to sludge external heat exchanger may also be employed to avoid process heat wasting.

Figure 3:
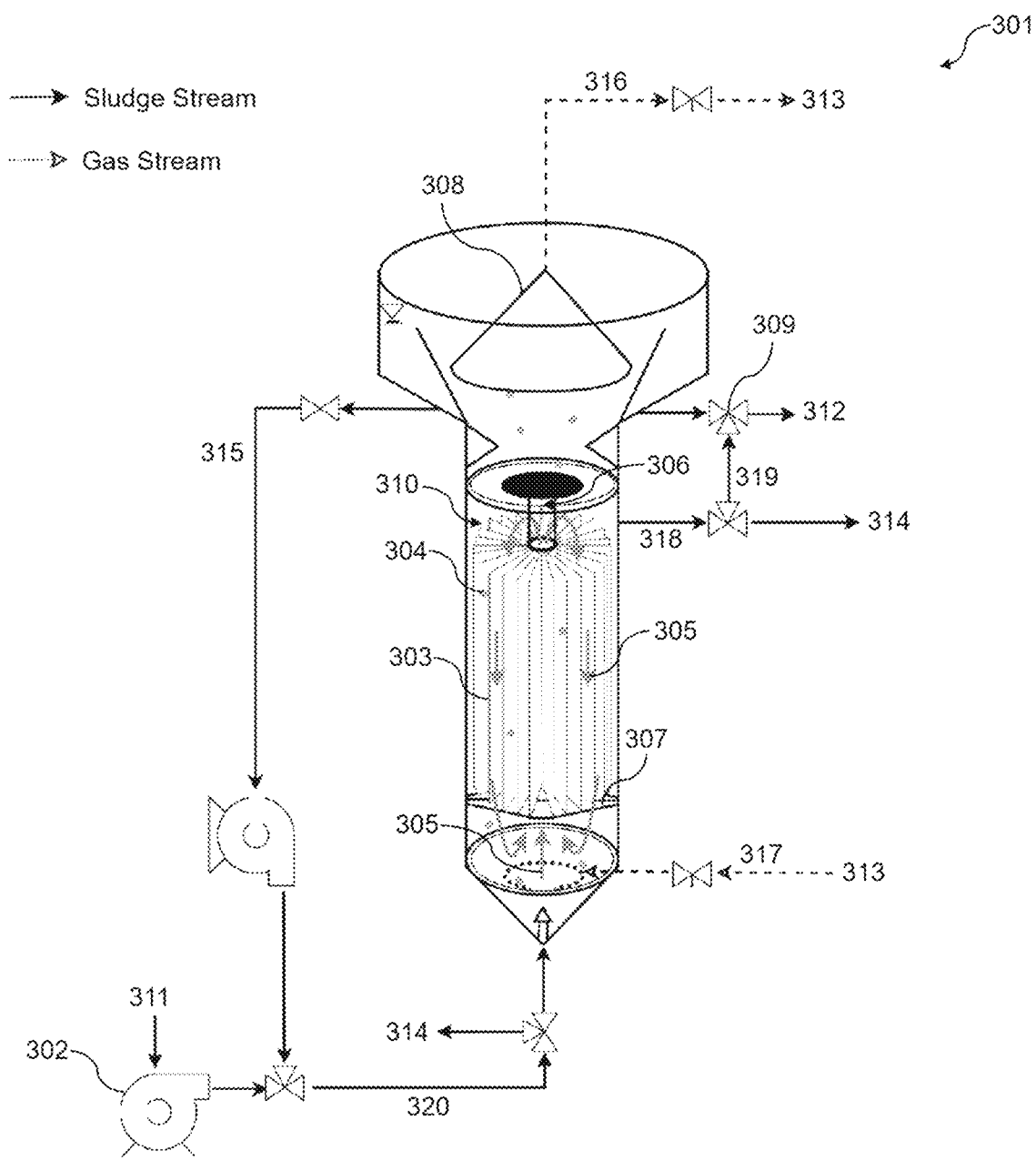
FIG. 3 is a schematic of a bioreactor with a fixed electroactive media design, according to some embodiments of the present disclosure.
Figure 5:
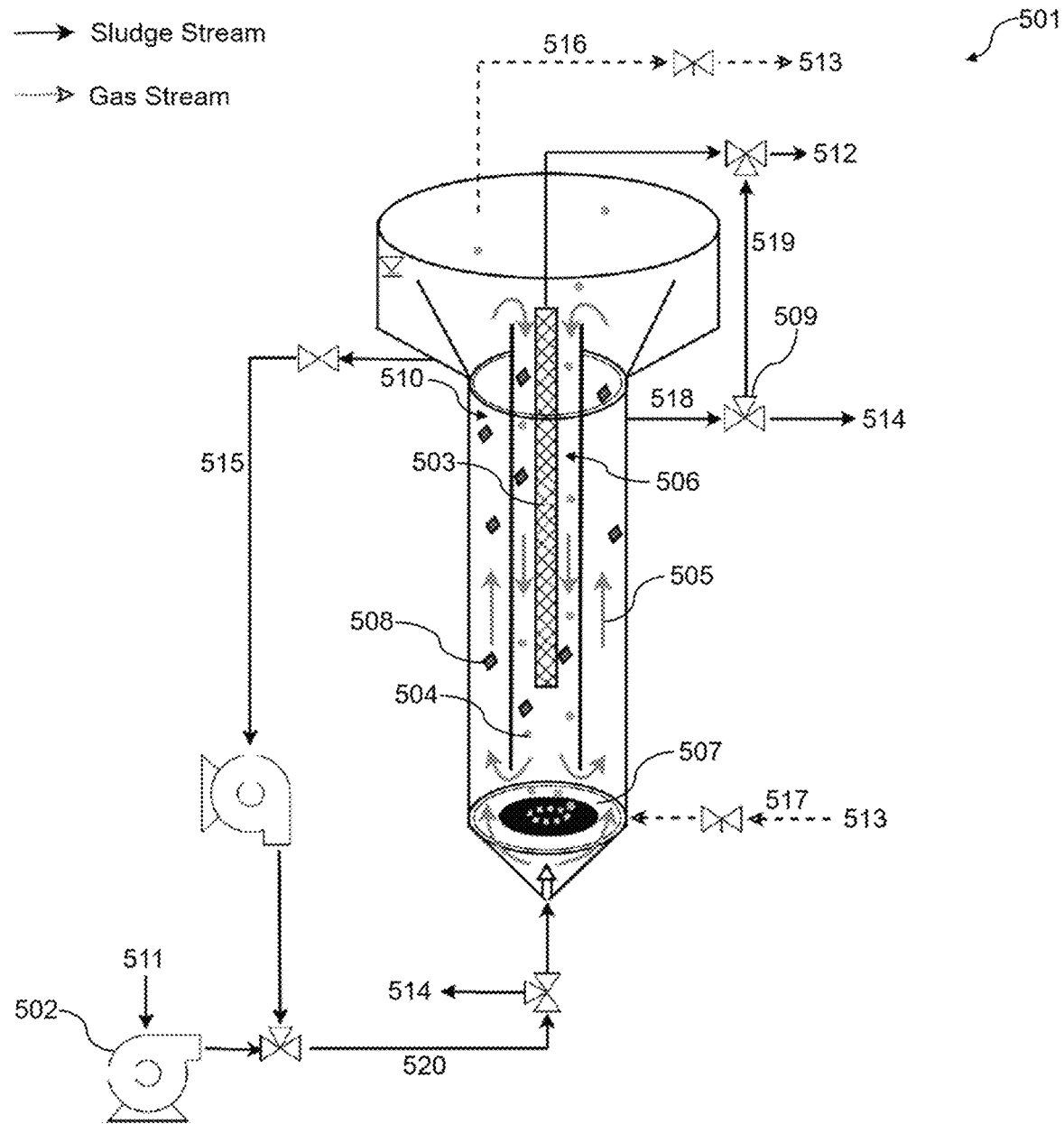
FIG. 5 is a schematic of a bioreactor having a loose electroactive media design, according to some embodiments of the present disclosure.

In some embodiments, bioreactor 202 can adopt a configuration of retrofit chambers in anaerobic digestion system 201. In some embodiments, bioreactor 202 can include one to five chambers. In some embodiments, the bioreactor can include three chambers. The chambers are shown in FIGS. 3, 5, and 6, and are sized so as to include working volumes between about 1 and 25% of the full scale AD. The chambers can be composed of vertical cylindrical vessels of height to diameter ratios between about two and five. The chambers may be connected to AD recirculation piping, or if bioreactor sludge flows are too high, tapped into AD feed and treated sludge lines. The environment of bioreactor 202 can be uniquely designed to meet syntrophic bacteria and methanogens' preferred growth conditions. In some embodiments, the temperature inside the bioreactor can be configured to about 20 to 80° C., about 30 to 70° C., about 40 to 80° C., about 20 to 60° C., or about 40 to 60° C. The pressure inside the bioreactor can be about 1 to 10 bar, about 2 to 8 bar, about 3 to 6 bar, about 1 to 6 bar, or about 4 to 10 bar. In some embodiments, bioreactor sludge pH can be configured to about 5.0 to 8.0, 6.0 to 8.0, or 6.5 to 8.5. Bioreactor 202 can form a biocatalyst based on the sludge, a methanogen, a syntrophic bacterium, and optionally an added electron-conductive supplement. Non-limiting examples of the electron-conductive supplement can be nano-sized magnetite, carbon fibers, or multi-wall carbon nanotubes.

Gas stream in anaerobic digestion system 201 can include bioreactor biogas stream 210, AD biogas stream 211, reused biogas stream 205 as a portion of overall generated biogas from bioreactor 202 and AD 203, and final output biogas stream 206. AD biogas stream 211 and bioreactor biogas stream 210 can be collected by biogas header 204. The reused biogas stream 205 leaves biogas header 204 and can be back injected into the bottom of the bioreactor to facilitate mixing within the bioreactor, penetration of nutrients into the biofilm growing on the electroactive media, and purification of reused biogas stream 205 to engender high methane content in final output biogas stream 206. In some embodiments, an externally-generated hydrogen can be used for back injection. Biogas can be mostly composed of carbon dioxide and methane, with trace amounts of hydrogen sulphide and other gases. Methane is a valuable component of biogas, and is produced by a partnership between methanogenic archaea and syntrophic bacteria. Modification of the anaerobic digestion microbiome composition and activity can increase methane production rate by 25%, while adsorptive capacities of media, in addition to the autotrophic methanogenic metabolisms, can increase the methane content of biogas beyond the status-quo of 50-60%. The amount of biogas required for injection of reused biogas stream 205 can be between 0.1% and 60% of biogas produced by an AD, depending on cumulative size of the bioreactors and whether intermittent or continuous backwash is required. A source of carbon dioxide gas, such as waste carbon dioxide from downstream biogas upgrading (not shown) may also be injected into the bottom of bioreactor 202 for removal and conversion to biomethane.

A high-rate consortium of DIET-based syntrophy can be grown and ripened on the electroactive media inside the disclosed bioreactor by ensuring a steady supply of LMWO. If LMWO are not present in sufficient quantities in the feedstock entering the AD system, a prior fermentation process can be optionally used for pre-conditioning of the feed. In some embodiments, bioreactor feed 209 can be composed of greater than about 10% soluble COD, preferably greater than about 25%. The VFA content of bioreactor feed 209 can be greater than about 2,000 mg/L, preferably between about 5,000 and 15,000 mg/L with a propionic to acetic acid ratio less than about 2.0, but preferably less than about 1.4. In some embodiments, the biodegradable COD of the fermentate feed sludge can be composed of up to about 80% ethanol, methanol, isopropanol, isobutanol or combination thereof. The optional fermentation process can be achieved either by way of a fermentation section upstream of the bioreactor or by addition of fermentative media to the bioreactor for contact with incoming sludge prior to, or in tandem with, contact with electroactive media.

In some embodiments, improvement of AD performance can be attained by scouring high-rate biofilm components including cells and extracellular polymeric substances (EPS) from ripened electroactive media in the bioreactor, forming a biocatalyst based on the biofilm components, and dosing the biocatalyst into the AD. In this embodiment, electroactive media scour can be periodically performed using a combination of liquid shear force and/or biogas injection, and dosed biocatalyst contains biofilm components, which can bioaugment the AD with electro-syntrophic methanogenic metabolisms. In some embodiments, the biofilm scour is performed by continuously gas injection and liquid shear forces, but at a lesser intensity. In some embodiments, a fraction of ripened loose electroactive media is allowed to pass from the disclosed bioreactor directly into the AD, which also provides AD bioaugmentation. In some embodiments, the disclosed anaerobic digestion system does not have a prescribed bioaugmentation step, but rather retains electroactive media and associated biofilm within the disclosed bioreactor while serving to modify the sludge stream passing through by adsorptively and autotrophically removing $CO_2$ and related species such as carbonic acid, bicarbonate and carbonate, as well as by adsorptively and heterotrophically removing low molecular weight portions of the feed COD.

Some bacteria can directly transfer electrons to methanogens instead of interspecies $H_2$/formate transfer. This cell-to-cell electron transfer mechanism allows the methane production from the reduced organic compounds in a thermodynamically and metabolically more efficient manner, which ultimately provides rapid conversion of organic wastes to methane. Methanogens that can directly accept electrons from other species are called electrotrophic methanogens. An interspecies electrical connection has been found to be important for DIET. Known bacteria involved in DIET can include Geobacter species capable of forming a biologically wired connection to methanogens by producing filamentous protein appendages called electrically conductive pili, known colloquially as e-pili or microbial nanowires. However, aggregation of species can be important for such electrical connection, which may be possible in some specific configuration of anaerobic processes, such as upflow anaerobic sludge blanket (UASB) reactor. The addition of non-biological conductive materials as electroactive media, such as activated carbon, char (including, but not limited to, biochar, hydrochar, wood, and boiler ash), carbon cloth, iron nano-particles, carbon nanotubes, etc., in methanogenic bioreactors can induce DIET-ability within a wide range of bacteria that cannot produce conductive pili or nanowires like Geobacter species. Known syntrophic partners within the firmicutes and proteobacteria as well as certain recently described candidate divisions can attach to the surface of these electroactive media and utilize them as electrical conduits for electron exchange. This approach can be metabolically more favorable since these electroactive media may alleviate the energy investment by microbes for the synthesis of these conductive pili. Two common bacterial marker genes associated with DIET are pilA and omcS, which code for an electrically conductive pilus and an outer-membrane c-type cytochrome. Different types of electroactive media may up or downregulate one or both of these genes. Such differential gene expression may be favorable for cultivating syntrophic bacteria and electrotrophic methanogens within the bioreactor itself, or alternatively, for enriching bioreactor EPS s in biologically-derived nanomaterials that can aid downstream AD consortia. Therefore, this approach can allow sustainable engineering of DIET based syntrophy in many configurations of anaerobic digesters. Favorable electroactive media characteristics can include mild conductivity, high specific surface areas, macroporous structures for biological colonization and micro-niche formation, adsorptive capacity for VFAs and bicarbonate, as well as high redox-active properties such as electron donating and accepting capacity. Favorable EPS characteristics include improved conductivities, improved electron donating and accepting capacities, and high protein contents with particular enrichment for aromatic amino acids such as tryptophan and tyrosine. An exemplary strategy for increasing expression of DIET enabling exopolymers and electron shuttles is the operation an optional fermentation section to increase the alcohol component of LMWO, which in turn stimulates DIET gene expression within syntrophic bacteria. This is a logical first step, as many electroactive cultures have been observed within anaerobic reactors treating wastewaters of brewing and distilling industries. A second exemplary strategy for increasing expression of DIET enabling exopolymers and electron shuttles, is the provision of electroactive additives such as ferrous minerals to an optional fermentation section and/or bioreactor 202 which can promote endogenous production of conductive EPSs by local bacteria, thereby extending DIET activity beyond the biofilm regions in direct contact with electroactive media itself by means of EPS detachment into the suspended phase, for downstream utilization in DIET relationships between syntrophic partners in the bulk sludge.

FIG. 3 is a bioreactor 301 using a fixed electroactive medium, according to some embodiments of the present disclosure. Bioreactor 301 can include a pump 302 to inject a feedstock 311. The feedstock may be derived from actual wastes, or may by synthetically produced from stocks of acetate, ethanol or other LMWO. Feedstock 311 can optionally combine with a recycle sludge 315 to form an injection sludge 320 and enter bioreactor 301 from the bottom. After injection, a sludge flow 305 can travel through a draft tube 306 to the top of bioreactor 301, most of sludge flow 305 can be deflected to an annular space 310 in bioreactor 301, where sludge flow 305 can meet a filter element 303. In some embodiments, filter element 303 can be made of electroactive media such as a carbon cloth, which can support methanogenic biofilm growth. A gas/liquid separator 308 can optionally be installed on top of the bioreactor to isolate biogas bubbles 304 from the sludge flow and form a bioreactor biogas stream 316, which can be delivered to a biogas header 313. Part of the sludge flow on top of bioreactor 301 can form recycle sludge 315. After biofilm growth and harvest from the electroactive media, a biocatalyst can be formed and included in a bioreactor sludge 312 to be dosed into the main anaerobic digester (AD). A two-way or three-way valve 309 can be installed along the sludge streams to control the flow direction. An output sludge 318 can be released to a drain 314 for maintenance. Under normal operation and especially following biofilm scour, output sludge 318 may be composed of higher biomass density and can form a syntroph-enriched sludge 319, which can be merged with bioreactor sludge 312 and dosed in to the AD. Biogas bubbles 304 in the bioreactor can come from several sources. The biogas can be generated from the biofilm on filter element 303, or from some suspended biomass (not shown in the figure) in sludge flow 305, or from a reused biogas stream 317 back injected via a ring-shaped diffuser 307 from biogas header 313. In some embodiments, biogas bubbles 304 can include an externally-generated hydrogen can be used for back injection.

The sludge stream inside and surrounding the disclosed bioreactor can include feedstock 311 and optionally recycle sludge 315, sludge flow 305 inside bioreactor 301, bioreactor sludge 312, output sludge 318, which can be merged with bioreactor sludge 312 as syntroph-enriched sludge 319 during a media harvest event. Sludge flow 305 can initially travels upwards into the bottom aperture of, and along the height of, draft tube 306 in the center. Once the sludge flow exits the draft tube it reaches the top of the bioreactor, where a small amount of the sludge flow leaves the bioreactor to merge with bioreactor sludge 312 to enter the AD, however the majority of the sludge flow can change direction upon exiting the top aperture of draft tube 306 and is directed downwards along filter element 303 by way of a baffle above the draft tube. Annular space 310 can be occupied by filter element 303 made of electroactive media to enable biofilm growth, the detail of which can refer to FIG. 4. When the sludge flow reaches the bottom of the annular space, it can be drawn back into the bottom aperture of draft tube 306, completing the circuitous mixing pattern. A sludge recycle system based on recycle sludge 315 can provide supplemental mixing flow as well as feed sludge dilution. In some embodiments, a heating equipment can be added for recycle sludge 315 to increase its temperature to a desired value. If scour and/or harvesting of biomass is desired, sludge and/or biogas flows can be increased and applied either periodically or continuously. Scour or harvesting of biofilm from filter element 303 can also be aided by addition of scrubber particles such as powdered activated carbon (PAC) or magnetite particles, while the biofilm activity may be aided and the biocatalyst formation can be enabled by addition of electron-conductive supplements. Other amendments may also be used to aid biocatalyst formation and biofilm activity, such as carbon nanotubes, carbon fibers, chitosan, polyaniline or trace metals.

The biogas stream inside and surrounding the disclosed bioreactor can include bioreactor biogas stream 316 collected from the bioreactor and delivered to the biogas header, and reused biogas stream 317 from biogas header 313. If bioreactor biogas stream 316 is not collected, bioreactor 301 can assume a simple top geometry. Reused biogas stream 317 can form part of biogas bubbles 304, which can rise upwards through annular space 310 and countercurrent to the sludge flow along filter element 303. Reused biogas stream 317 can also promote mixing and mass transfer, aid in biofilm scour and harvesting from the electroactive media, and provide excess substrate for autotrophic prokaryotes including homoacetogens and $CO_2$ reducing methanogens.

Figure 4A:
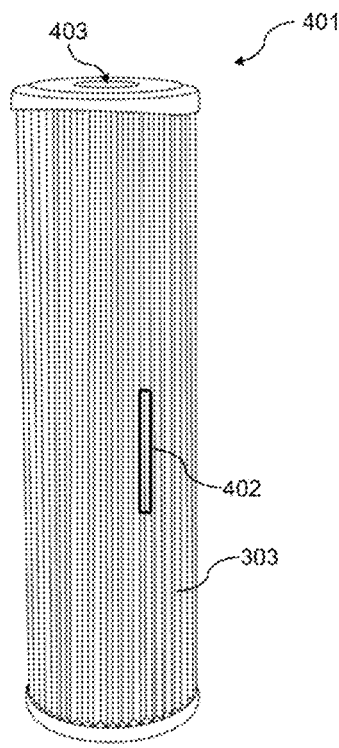
FIG. 4A is a perspective view of pleated filter element to support fixed electroactive media, according to some embodiments of the present disclosure.

When bioreactor 301 is configured as a vertical column configuration as depicted in FIG. 3, filter element 303 can adopt a pleated or lobate cylindrical arrangement and fitted inside the bioreactor column, a filter device 401 with such an arrangement is shown in FIG. 4A. In case of a pleated configuration as illustrated in bioreactor 301, biogas bubbles 304 and sludge flow 305 can travel between and along the pleats of filter element 303, without trans-membrane permeation. Filter element 303 can be located in the annular space and is wound around the draft tube, and hosts electrosyntrophic biofilms. Filter element 303 can be made of electroactive media such as carbon cloth, which can be the site of rapid methanogen biofilm growth. As sludge flow 305 is forced down along the vertical axis of the electroactive media it can encounter biogas bubbles 304 rising through the liquid, which can be injected directly into annular space 310. This can allow counter-current gas exchange, providing an ample concentration of carbon dioxide to methanogens growing on the electroactive media, the carbon dioxide can then be transformed into methane or adsorbed to the media surface.

When sludge flow 305 reaches the bottom of the annular space, it can become re-incorporated into the draft tube, promoting circuitous flow. The carbon cloth material used as the electroactive media promotes the DIET metabolism over other methanogenic metabolisms, as the mildly conductive material is able to accept electrons from electroactive syntrophic bacteria and donate these electrons to electroactive methanogenic archaea. This symbiotic sharing of electrons is more thermodynamically favorable than alternative metabolic pathways, and as such these methanogens can dedicate more energy to cell growth and division, which in turn results in greater methanogen abundance and methane production potential.

The electroactive syntrophic bacteria used for the instant disclosure can include, but are not limited to, members of the Proteobacteria, Firmicutes and Coprothermobacteraeota phyla including the families Syntrophomonadaceae, Ruminococcaceae, Peptococcaceae, Syntrophaceae, Hydrogenophilaceae, Defluviitaleaceae and Coprothermobacteraceae, and members of the families Desulfobulbaceae and Anaerolinaceae and microorganisms belonging to the genera *Geobacter, Shewanella, Desulfovibrio, Clostridium*. The methanogenic archaea used for the instant disclosure can include, but are not limited to, the families Methanobacteriaceae, Methanomassiliicoccaceae, Methanosaetaceae, Methanosarcinaceae, and Methanothermobacteraceae.

A low sludge flow circulation velocity can allow deep methanogenic biofilms to grow on the electroactive media, while biogas bubbles 304 can aid in the mixing of the sludge within the disclosed bioreactor and facilitate penetration of nutrients into the biofilm matrix. The bioreactor can operate in four phases: growth, harvest, biocatalyst formation, and dosing. The growth phase can allow thick biofilms to be produced on the electroactive media. The harvest phase can involve removal of these biofilms via hydrodynamic of sludge flow 305 and/or biogas bubble 304-based scour. Scouring of the element can increase the velocity of sludge flow so that the liquid shear force overcomes biofilm adhesion forces. Scrubber particles which increase shear may be added to aid in this phase. During the harvest phase, the pump rate of recycle sludge 315 can be increased. Up to 60% of the biofilm biomass may be scoured from the media during a harvest event. Once the biofilm is harvested from the electroactive media, the circuitous liquid velocity can be reduced and the biocatalyst formation phase can be initiated. Biocatalyst formation is an optional phase and can be propagated by injecting an electron-conductive supplement into the bioreactor so that it interfaces with the sloughed biofilm sludge accumulated in the annular space. These electron-conductive supplements can functionally replace the carbon cloth electroactive media.

Optionally, one or more coagulant chemicals can be injected into the harvested biofilm to promote cohesion of harvested biomass and inclusion of conductive amendments, forming the mature biocatalyst. The last phase can involve the dosing of all of the biocatalyst through output sludge 318 to bioreactor sludge 312 as syntroph-enriched sludge 319 into the AD. Each four-phase cycle of the bioreactor can last about 1 to 30 days, about 2 to 20 days, about 4 to 30 days, about 1 to 14 days, or about 4 to 14 days, which can depend on the type of sludge feed, microbiology in the bioreactor, temperature and other conditions. Over time, successive dosing of biocatalyst to the AD can result in the accumulation of biocatalyst therein, as AD retention times can average at about 30 days.

FIGS. 4A-D further illustrate filter element 303 and a filter device 401 housing the filter element, according to some embodiments of the present disclosure. FIG. 4A depicts filter device 401 with filter element 303 in a pleated configuration. In some embodiments, non-pleated and flat planar lobes can also be used. Filter element 303 can be made of electroactive media such as carbon cloth. The pleated carbon cloth can be made as a replaceable container such as a cartridge, which can sit above the ring-shaped diffuser at the bottom of the bioreactor. The carbon cloth filter element 303 can be vertically positioned along the entire length of the annular space, and pleated so as to increase its surface area. The inner core 403 of filter device 401 can wrap around the draft tube inside the bioreactor. For purpose of longevity, the carbon cloth can be quilted upon support material prior to pleating. The pleated carbon cloth can have a high pleat pitch and deep pleat height, which can result in decreased number of pleats for balance between high surface area and element headloss. The distance between pleat or lobe edges at the perimeter of the fixed media element may be from about 5 to 50 cm apart, about 10 to 45 cm apart, about 15 to 40 cm apart, about 20 to 35 cm apart, about 25 to 30 cm apart, about 25 to 50 cm apart, or about 5 to 30 cm apart. The pleat or lobe angles can be from about 5 to 30 degrees, about 10 to 25 degrees, about 15 to 20 degrees, about 5 to 20 degrees, or about 15 to 30 degrees. Non-pleated versions of filter element 303 include lobate arrangements, where each lobe face is fixed to the inner core 403. When pressure drop reaches a set point, it can trigger an automatic scour for biofilm harvest and restoration of hydraulic conductivity.

Figure 4B:
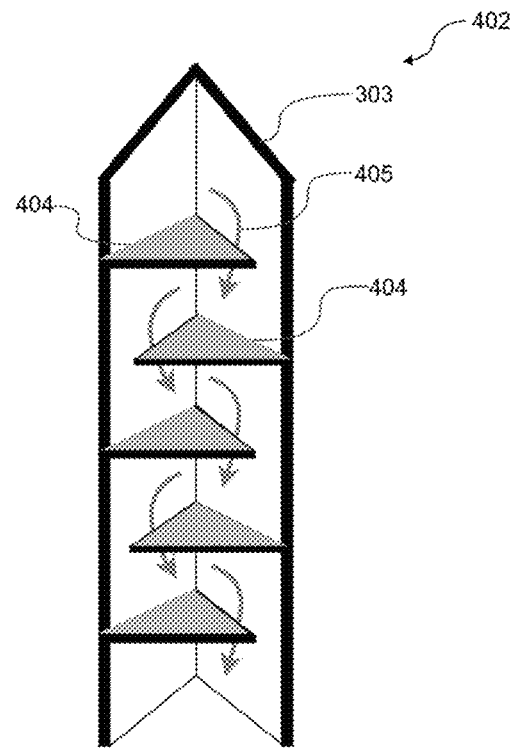
FIG. 4B is an expanded view of two adjacent pleated filter elements, according to some embodiments of the present disclosure.

FIG. 4B depicts an expanded view 402 of adjacent filter elements in a pleat configuration. A crevice baffle 404 can be placed in a staggered pattern between adjacent filter elements. Crevice can refer to the space between pleats or lobes. For example, a first crevice baffle can be attached to an observer's left side of the crevice, the next crevice baffle can be attached to an observer's right side of the crevice. The distribution of crevice baffles 404 can follow in this way throughout the whole height of filter element 303 in filter device 401. Crevice baffle 404 can enhance mixing, increase surface area, and prevent short-circuiting. A sludge flow 405 disrupted by crevice baffle 404 can lead to an improved mixing. In some embodiments, crevice baffle 404 can be made of carbon cloth or carbon fiber bristles. In some embodiments, crevice baffles are not used, where instead an S-shaped curving of media lobes is employed throughout the height of the lobes, with the curve of each lobe nested within that of the neighbouring lobe, so that flow follows a similar S-shaped path as illustrated in FIG. 4B.

Figure 4C:
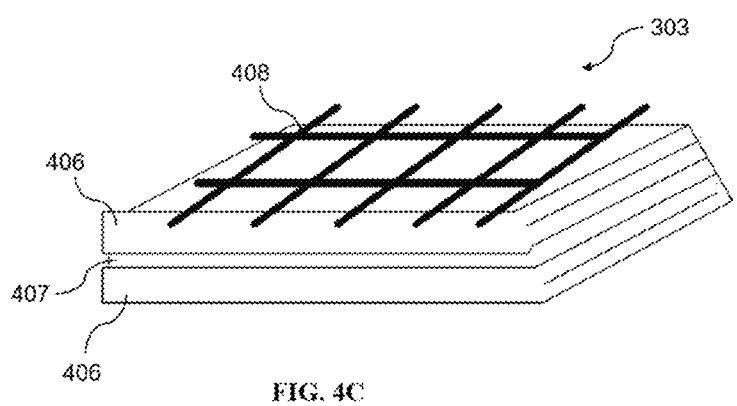
FIG. 4C is a perspective view of carbon cloth filter element, according to some embodiments of the present disclosure.

FIG. 4C depicts a perspective view of filter element 303, according to some embodiments of the present disclosure, which can be made of a double-weave activated carbon cloth 406 quilted onto a basal support 407. The basal support can be made of a woven stainless steel or of inert nylon, polyurethane or polyethylene. A screen 408 can be optionally placed on the surface of carbon cloth 406 to provide turbulent flow tangential to surface for enhanced mass transfer, as well as additional support for purpose of longevity. Non-limiting materials to make screen 408 can include, but not limited to steel, nylon, polyurethane, polyethylene, polycarbonate, and polypropylene. The filter element can be pleated then sewn end to end so as to form a cylindrical star or polygram type shape. In some embodiments, fixed media elements may be connected to an electrical circuit, such that a voltage potential between about 0.1 and 2 volts can created across the media element. In such embodiments, carbon cloth 406 on one side becomes a biologically active cathode for sustaining electromethanogenesis, while 407 becomes a proton exchange membrane, while carbon cloth 406 on the other side facilitates anodic reactions. The addition of an electrical circuit to fixed media elements enables introduction of exogenous electrons for autotrophic electromethanogenic reduction of carbon dioxide to methane, wherein electricity supply can be from a utilities grid or from local power generated on-site.

Figure 4D:
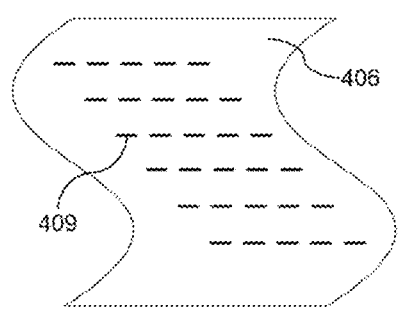
FIG. 4D is a perspective view of a carbon cloth, according to some embodiments of the present disclosure.

FIG. 4D depicts an embodiment of carbon cloth 406 used for filter element 303. The carbon cloth can be chemically enhanced. The chemical enhancement can involve bonding a conductive nano-material 409 to the surface for greater electroactive cell density and possibly prolonged activity in the sloughed biofilm. The conductive nano-material 409 can include, but not limited to, carbon nanotube and chitosan, which can aid microbial attachment and symbiosis. The conductive nano-material can be attached onto the surface of the carbon cloth using chemical vapor deposition or other methods via different configurations including, but not limited to, dot, line, and random distribution.

In some embodiments, instead of electroactive fixed media such as carbon cloth, non-electroactive media panel can be used (not shown in the figures). An electroactive foaming paint may be sprayed or painted and cured upon the media panels prior to assembly, thereby providing macroporous structures with electroactive properties. Non-limiting examples of non-electroactive media panel can include, but not limited to, polymeric panels such as polyurethane or polyethylene panels used in conventional crossflow and vertical flow fixed media.

FIG. 5 depicts a bioreactor 501 using a loose electroactive medium, according to some embodiments of the present disclosure. There can be several differences in the configuration and operation process between bioreactor 501 and 301. Bioreactor 501 uses electroactive media in loose form for biofilm growth, while bioreactor 301 uses electroactive media in a fixed form. The use of loose electroactive media in bioreactor 501 can range in size from about 0.5 to 50 mm diameter. Such loose electroactive media can be accompanied by a filter element such as a membrane or a sieve, which can allow sludge permeation but block the loose electroactive media, such that the treated sludge can be delivered out of the bioreactor while leaving the loose electroactive media inside the bioreactor for continuous biofilm growth. In addition, the flow pattern of sludge and gas streams are reversed, the countercurrent encounter between sludge flow and biogas bubbles occurs in the draft tube in bioreactor 501, while the annular space is where this countercurrent encounter occurs in bioreactor 301.

Bioreactor 501 can include a pump 502 to inject a feedstock 511 which may be composed of sludge, fermented sludge, or synthetic wastewater containing acetate, ethanol or other LMWO. Feedstock 511 can optionally combine with a recycled sludge 515 to form an injection sludge 520 and enter the bioreactor from the bottom. After injection, the injection sludge can become a sludge flow 505, which can travel through an annular space 510 to the top of the bioreactor, most of sludge flow 505 can be deflected into a draft tube 506 in the bioreactor, where sludge flow 505 can meet a filter element 503. A fraction of the sludge flow at the top of the bioreactor can be released as a recycled sludge 515. The filter element can collect a bioreactor sludge 512, optionally containing biofilm generated from a loose electroactive medium 508 to be dosed into the main anaerobic digester (AD). The entire biofilm coated loose electroactive medium 508 may be extracted in a loose media-containing sludge 518 leaving the bioreactor to be dosed through a syntroph-enriched sludge 519 and on to bioreactor sludge 512 entering the AD. A two-way or three-way valve 509 can be installed along the sludge streams to control the flow. For maintenance purposes, loose media-containing sludge 518 can be wasted to a drain 514. Biogas bubbles 504 in bioreactor 501 can be collected as a bioreactor biogas stream 516, delivered to a biogas header 513. A fraction of the biogas from biogas header 513 can be back injected into bioreactor 501 as a reused biogas stream 517. In some embodiments, biogas bubbles 504 can include an externally-generated hydrogen can be used for back injection. A biogas diffuser 507 can channel the biogas injection to draft tube 506 only, which can provide countercurrent biogas flow relative to sludge flow 505.

The sludge stream inside and surrounding the disclosed bioreactor 501 can include feedstock 511 and optionally recycled sludge 515, sludge flow 505 inside the bioreactor, bioreactor sludge 512 after treatment in the bioreactor, loose media-containing sludge 518, which can form syntroph-enriched sludge 519 to be merged with bioreactor sludge 512 or wasted to drain 514 for maintenance purposes. Sludge flow 505 can initially travel upwards through annular space 510 to the top of the bioreactor. In some embodiments, the sludge flow is released as waste sludge to drain 514 for maintenance purposes. As a typical dosing operation, part of loose media-containing sludge 518 can be released as syntroph-enriched sludge 519 to merge with bioreactor sludge 512 released from the bioreactor and dosed into the AD. In some embodiments, part of the sludge flow can form recycled sludge 515. A sludge recycle system based on recycled sludge 515 can provide supplemental mixing flow as well as feed sludge dilution. In some embodiments, a heating equipment can be added for recycled sludge 515 to increase its temperature to a desired value. The majority of the sludge flow can change direction upon reaching the top of annular space 510 and is directed downwards along the draft tube by way of a baffle. Draft tube 506 can host filter element 503, which can withdraw sludge from the bioreactor to form bioreactor sludge 512 while leaving loose electroactive media 508 behind. When the sludge flow reaches the bottom of the draft tube, it can be drawn back into the bottom of the annular space, completing the circuitous mixing pattern. Such mixing patterns can enhance removal of excess biofilm and attached micro-bubble biogas, both of which can decrease particle density and result in undesired media behavior.

The biogas stream inside and surrounding the disclosed bioreactor can include bioreactor biogas stream 516 collected from the bioreactor and delivered to biogas header 513, and reused biogas stream 517 from the biogas header. Reused biogas stream 517 forms biogas bubbles 504, which rise upwards through draft tube 506 and countercurrent to the sludge flow along filter element 503. Reused biogas stream 517 can also promote mixing and mass transfer, aid in biofilm scour and harvesting from the electroactive media, and provide excess substrate for $CO_2$ reducing methanogens.

Non-limiting examples of filter element 503 can include, but not limited to, a sieve and membrane. Non-limiting examples of loose electroactive media 508 can include, but not limited to, biochar, loose activated carbon, magnetic mineral, and magnetic ferric oxide particles. The magnetic ferric oxide particles can be in nano, micro, or mm size with mild electro-conductivity. The loose electroactive media can be used for high carbon dioxide adsorption capacity. Filter element 503 can be used to allow high loading of the loose electroactive media 508 in compact configuration and retention of the loose electroactive media in the bioreactor. Auto-pressurization can be employed to enhance carbon dioxide absorption to the liquid phase, carbon dioxide adsorption to the loose electroactive media, and flux across membrane. The pressure inside the bioreactor can be about less than about 2, 5, 7, or 10 bar.

Sludge flow 505 and the slurry of loose electroactive media 508 can follow a reverse flow-pattern compared to the previously described fixed electroactive media embodiment in FIG. 3. If longer biogas contact time is required, the countercurrent sludge flow 505 can be increased to extend holdup of biogas bubbles 504. A three-phase separator (not shown in the figure) can allow recirculation of only sludge flow from the mixture while the recycled sludge 515 into the bottom of the bioreactor to provide supplemental mixing flow and dilution of injection sludge 520. The biofilm activity on loose electroactive media 508 can be aided by addition of electron-conductive supplements such as carbon nanotubes, chitosan, carbon fiber, polyaniline or trace metals. In some methods of biocatalyst dosing, there can be periodic dosing of entire loose media via loose media-containing sludge 518 to the AD. In other embodiments, some biofilm can find its way into the AD during regular operation through filter element 503 in low mixing velocities.

Figure 6A:
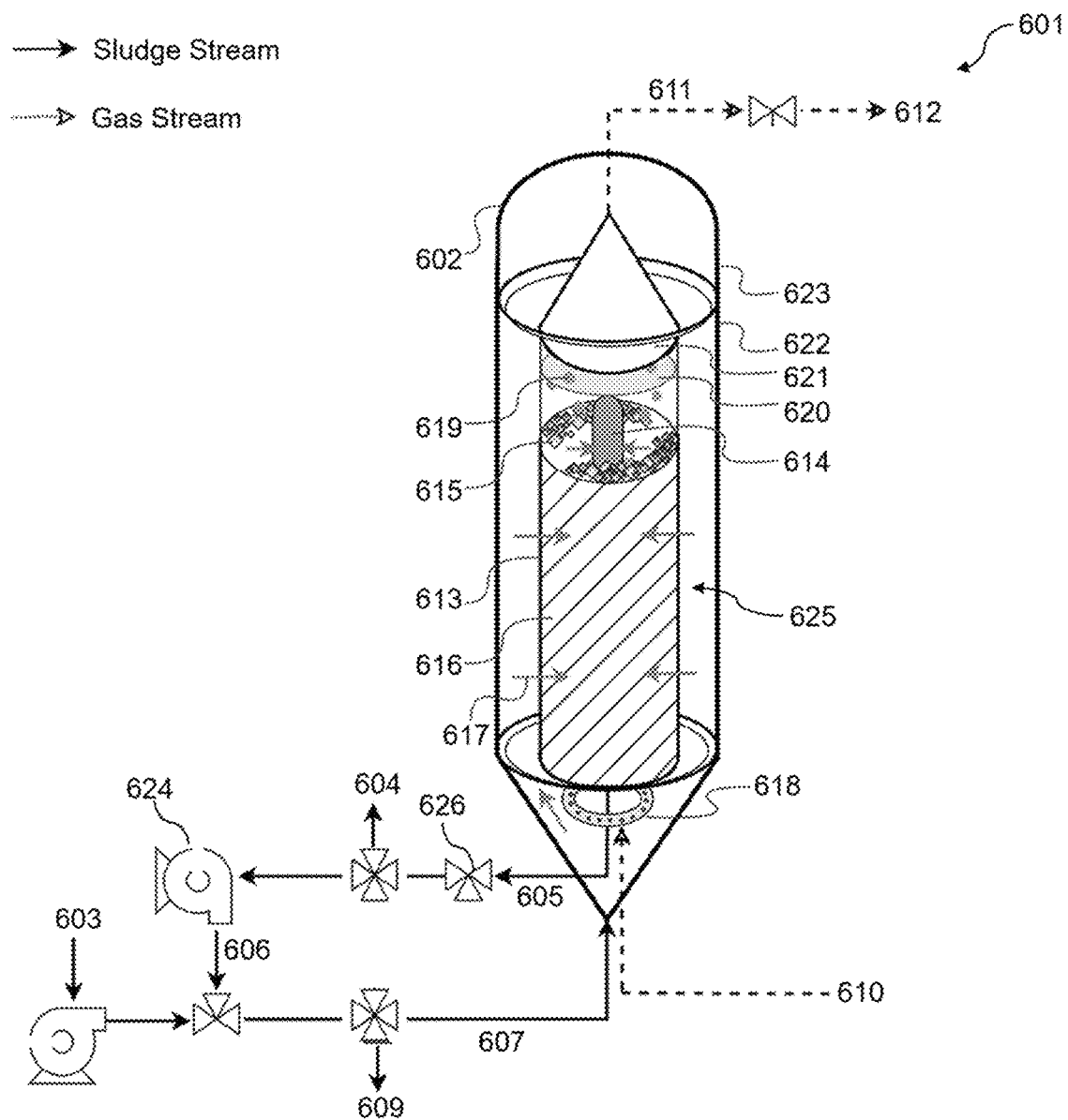
FIG. 6A is a schematic of a bioreactor having a cartridge design in an operating mode, according to some embodiments of the present disclosure.

In some embodiments, a loose electroactive medium in the present disclosure can be placed inside a container including, but is not limited to, cartridge, porous receptacle, and tea bag. In some embodiments, the container can be replaceable. FIG. 6A depicts a bioreactor 601 using a loose electroactive medium in a container such as a cartridge configuration in an operating mode, according to some embodiments of the present disclosure Similar to the embodiment shown in FIG. 5, bioreactor 601 also relies on loose electroactive media. However, the loose electroactive media in this embodiment are contained in a container such as a cartridge, which can be conveniently replaced. The loose electroactive media can occupy the cartridge at about 10 vol % to 90 vol %, and range in size from about 0.5 to 50 mm in diameter.

Bioreactor 601 can include an outer housing 602 composed of a removable head cap 623 and a lower section 622. Removable head cap 623 can be secured upon lower section 622, which can enable convenient replacement of an electroactive media container 613. A pump 624 can be used to inject a feedstock 603 to form an injection sludge 607 into an annular space 625 formed between electroactive media container 613 and outer housing 602. Electroactive media container 613 can be made of an outer barrier wrap 616 hosting loose electroactive media 615 and a sludge collection tube 614. The sludge after injection into annular space 625 can form a sludge flow 617 passing through outer barrier wrap 616 to enter into electroactive media container 613 and contact electroactive media 615, where biofilm formation occurs. Generated biogas bubbles 619 can travel through a gas permeable screen 620 into a gas collector 621, which can form a bioreactor biogas stream 611 and delivered to a biogas header 612. Gas permeable screen 620 can release the generated biogas while keeping loose electroactive media 615 inside the bioreactor. A fraction of the biogas from biogas header 612 can be back injected into bioreactor 601 as a reused biogas stream 610. A diffuser 618 can make sure the biogas or carbon dioxide are injected into the bottom of the container media for mixing, backwashing, biofilm scouring, and/or adsorption of gas components. In some embodiments, an externally-generated hydrogen can be used for back injection. Gas input may be continuous or intermittent, and can be important to prevent media caking or channeling. A treated sludge 605 can be released from bioreactor 601. A two-way or three-way valve 626 can be installed along the sludge streams to control the flow. Biogas may be injected during backwashing, to enhance separation of biomass from media particles, and to help ameliorate media bed channeling. Alternatively, waste carbon dioxide gas from downstream biogas upgrading (not shown) can be used for backwashing. Under normal operation conditions, a bioreactor sludge 604 can be delivered into the AD for further digestion. A recycled sludge 606 can be back merged with feedstock 603 to dilute the feed strength. A waste sludge 609 can be discharged to drain, for purpose of maintenance or container replacement.

The sludge stream inside and surrounding the disclosed bioreactor 601 can include injection sludge 607 formed by feedstock 603 and optionally recycled sludge 606, sludge flow 617 inside the bioreactor, treated sludge 605, bioreactor sludge 604, and waste sludge 609 for maintenance purposes. Sludge flow 617 can travel from annular space 625 through outer barrier wrap 616 and enter electroactive media container 613, where the sludge, the biogas, and the loose electroactive media encounter and form biofilm. Sludge collection tube 614 then collects the sludge and forms treated sludge 605. In some embodiments, part of treated sludge 605 can be discharged as bioreactor sludge 604 and delivered into the AD. In some embodiments, part of treated sludge 605 is recycled as recycled sludge 606 and merged with feedstock 603 for back injection to the bioreactor. Waste sludge 609 can be discharged to the drain, for purpose of maintenance or container replacement.

The biogas stream inside and surrounding the disclosed bioreactor can include bioreactor biogas stream 611 collected from the bioreactor and delivered to the biogas header, and reused biogas stream 610 from the biogas header. Reused biogas stream 610 forms biogas bubbles 619, which rise upwards through electroactive media container 613. Reused biogas stream 610 can also promote mixing and mass transfer, aid in biofilm scour and harvesting from the electroactive media, and provide excess substrate for $CO_2$ reducing methanogens.

Figure 6B:
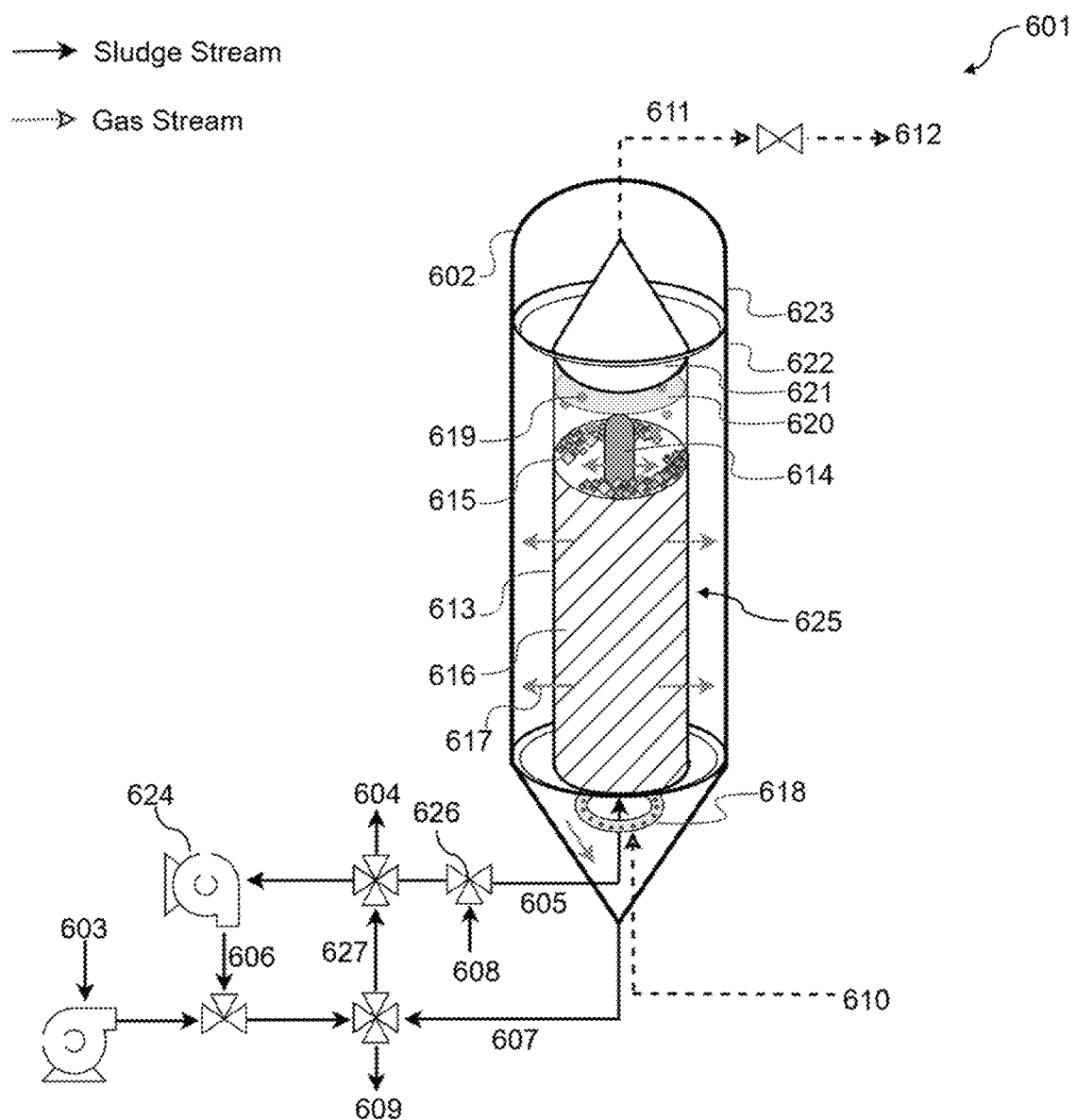
FIG. 6B is a schematic of a bioreactor having a cartridge design in a backwashing mode, according to some embodiments of the present disclosure.

FIG. 6B depicts a bioreactor 601 using a loose electroactive medium in a container such as a cartridge configuration in a backwashing mode, according to some embodiments of the present disclosure. Compared to the operating mode as illustrated in FIG. 6A, a flow of clean water or nutrient solution, or electroactive nanoparticle solution is injected for backwashing, provided valve 626 is positioned to allow flow from backwash injection stream 608 for travel along 605, which is a reversal of normal operative flow. Backwash liquor can then exit the bottom of the vessel as injection sludge 607, which can then travel as stream 627 to be dosed to the AD, in this case bioreactor sludge 604 can be used as a backwash liquor for the AD.

Figure 7A:
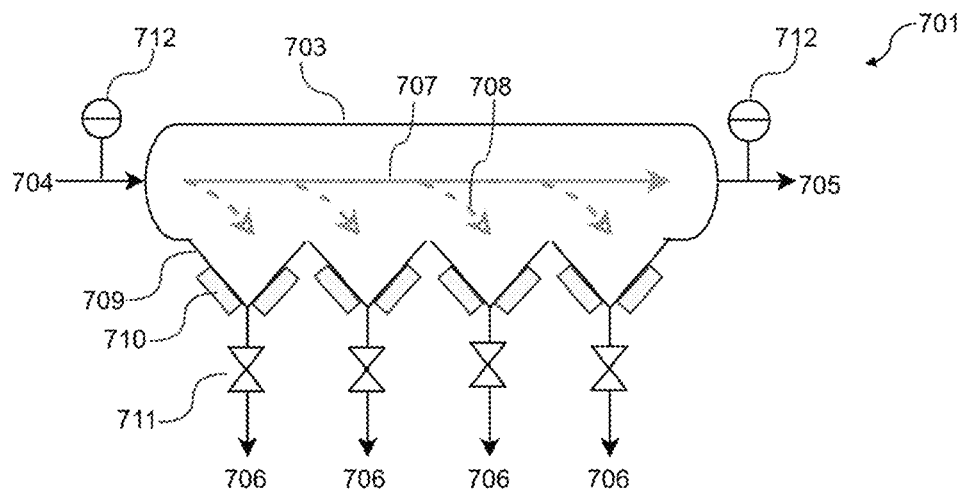
FIG. 7A is a schematic of a first configuration of a magnetic media recycler, according to some embodiments of the present disclosure.
Figure 7B:
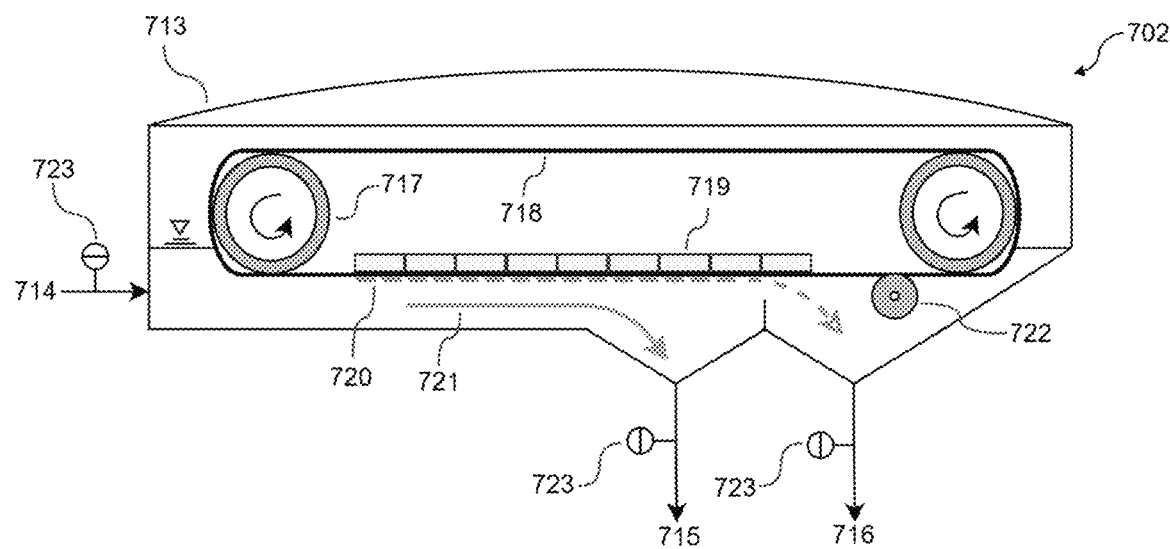
FIG. 7B is a schematic of a second configuration of a magnetic media recycler, according to some embodiments of the present disclosure.

FIGS. 7A-B show different configurations of recyclers to collect magnetic media, according to some embodiments of the present disclosure. In some embodiments when magnetic loose electroactive media are used in the bioreactor, a magnetic media recycler can be used downstream to collect the loose electroactive media. The magnetic media recycler can be located at bioreactor sludge discharge to prevent the magnetic media from entering the AD, and recycling the magnetic media back to the bioreactor. In some embodiments, the recycler can be placed at the AD discharge, the magnetic media can flow from the bioreactor to the AD and then collected by the recycler. In some other embodiments, the recycler can be placed at both the bioreactor discharge and the AD discharge, such that a full collection of the magnetic media can be achieved.

FIG. 7A shows a flow-through recycler 701 including a flow-through vessel 703, a media collector boot 709, an electromagnet 710, a valve 711 to control the sludge flow, and a sensor 712 to measure the magnetic media capture efficiency, loss and inventory. Electromagnets 710 can have an oscillating polarity or on/off cycle to isolate magnetic media while still allowing entrainment. In some embodiments, sensor 712 can be a Hall-effect ferrous particle sensor.

The sludge flows surrounding flow-through recycler 701 can include a sludge feed 704 injected into flow-through recycler 701. Under the magnetic effect of electromagnets 710, the sludge flow can be separated into a magnetic media free sludge flow 707 and a magnetic media rich sludge flow 708. In some embodiments, electromagnets 710 can have an oscillating polarity or on/off cycle to separate magnetic media from the bulk sludge flow while still allowing entrainment, resulting in formation of magnetic media rich stream in a recycled sludge 706. Magnetic media free sludge flow 707 can form a sludge output 705 which can be substantially free of magnetic media. Magnetic media rich sludge flow 708 can flow through media collector boot 709 and form a recycled sludge 706 and delivered back into the bioreactor or AD, depending on where the recycler is located. Sludge feed 704 can be from bioreactor or AD, which can be rich in magnetic media with associated electroactive biomass and biofilm. Sludge output 705 which is substantially free of magnetic media after treatment in the recycler can be delivered into the AD (if flow-through recycler 701 is placed at the bioreactor discharge) or to drain/dewatering (if flow-through recycler 701 is placed at the AD discharge).

FIG. 7B shows a suspended conveyer recycler 702 including a vessel housing 713, a conveyer wheel 717, a conveyer belt 718, an electromagnet 719, a foulant removal unit 722, and a sensor 723 to measure the magnetic media capture efficiency, loss and inventory. In some embodiments, sensor 723 can be a Hall-effect ferrous particle sensor. Foulant removal unit 722 can be a brush or scraper to facilitate removal of foulant from the surface of the conveyor belt after the belt has transited past the electromagnets 719, and separated magnetic electroactive biomass has been released to form a recycled sludge 716. In some embodiments, the material of the conveyer belt 718 itself can be non-magnetic, while allowing unobstructed flux of magnetic fields from electromagnets 719 into the bulk sludge.

The sludge flows surrounding suspended conveyer recycler 702 can include a sludge feed 714 injected into suspended conveyer recycler 702. Under the magnetic effect of electromagnets 719, the sludge flow can be separated into a magnetic media rich sludge flow 720 and a magnetic media free sludge flow 721. Magnetic media free sludge flow 721 can form a sludge output 715 which can be substantially free of magnetic media. Magnetic media rich sludge flow 720 can form a recycled sludge 716 and delivered back into the bioreactor or AD, depending on where the recycler is located. Sludge feed 714 can be from bioreactor or AD, which can be rich in magnetic media with associated electroactive biomass and biofilm. Sludge output 715 which is substantially free of magnetic media after treatment in the recycler can be delivered into the AD (if conveyor recycler 702 is placed at the bioreactor discharge) or to drain/dewatering (if conveyor recycler 702 is placed at the AD discharge). If conveyor recycler 702, or flow-through recycler 701, are placed to collect magnetic media and associated biomass discharged from the AD, recycler sizing can be increased to match AD discharge flow, and thus the total inventory of magnetic media can also be increased, resulting in greater decentralized media capacity within the anaerobic digestion system compared to locating the recycler at the bioreactor discharge.

Figure 8A:
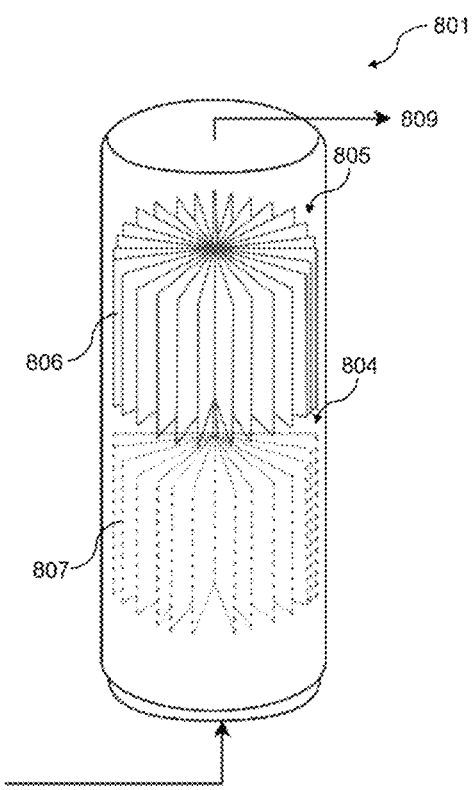
FIG. 8A is a schematic of a first configuration of a bioreactor integrating a fermentation process, according to some embodiments of the present disclosure.
Figure 8B:
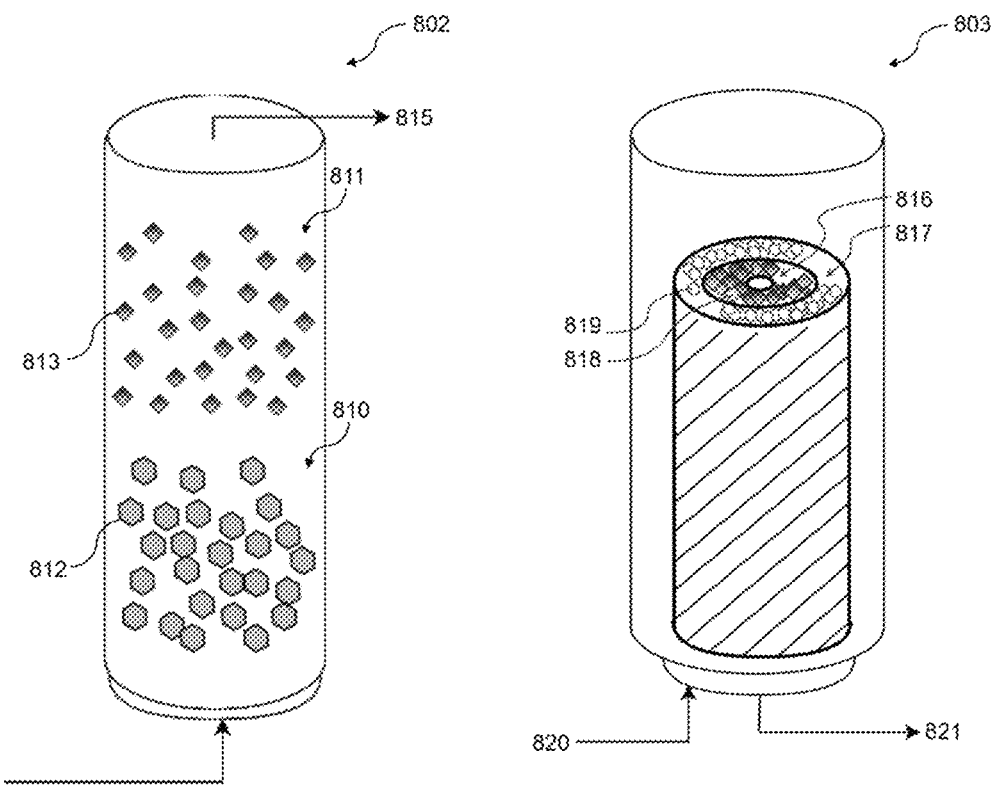
FIG. 8B is a schematic of a second configuration of a bioreactor integrating a fermentation process, according to some embodiments of the present disclosure.
Figure 8C:
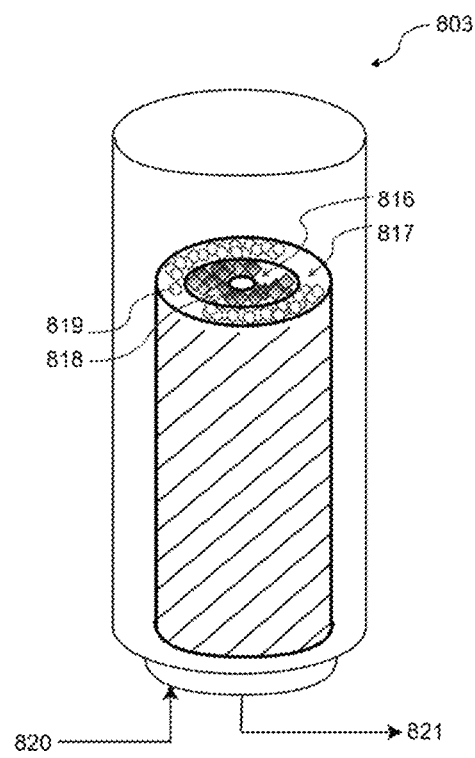
FIG. 8C is a schematic of a third configuration of a bioreactor integrating a fermentation process, according to some embodiments of the present disclosure.

FIGS. 8A-C are embodiments of the present disclosure which integrate the fermentation process and the biocatalyst formation process inside one bioreactor. As a result, a separate fermentation vessel is not utilized. Such a bioreactor can be a fixed media bioreactor 801, a loose media bioreactor 802, or a cartridge bioreactor 803. Fixed media bioreactor 801 can be composed of a fermentation section 804 and a biocatalyst formation section 805. Fixed media bioreactor 801 can take a sludge feed 808, which can undergo fermentation in a fixed fermentation media 807 toward a sufficient concentration of LMWO, which is suitable for the biocatalyst formation on fixed electroactive media 806. Non-limiting examples of fixed electroactive media can include, but not limited to, carbon cloth and RVC. The fixed fermentation media and the fixed electroactive media can adopt a pleated cylindrical arrangement. The fermentation media can be amenable to dissimilatory iron reducing bacteria, some of which also possess electro-syntrophic metabolism. An output sludge 809 can be formed and dosed into the AD.

Loose media bioreactor 802 can be composed of a fermentation section 810 and a biocatalyst formation section 811. Loose media bioreactor 802 can take a sludge feed 814, which can undergo fermentation on loose fermentation media 812 toward a sufficient concentration of LMWO, which is suitable for the biocatalyst formation on loose electroactive media 813. Non-limiting examples of fixed electroactive media can include, but not limited to, biochar, activated carbon, metal nano-particles, carbon nanotubes, and chitosan or polyaniline activated materials. The fermentation media can be amenable to dissimilatory iron reducing bacteria, some of which also possess electro-syntrophic metabolism. The loose fermentation media can be of greater density than the loose electroactive media. Such arrangements enable sludge feed 814 to contact the loose fermentative media first for a fermentation process, resulting in both fermentation and biocatalyst formation steps occurring on separate media, yet in the same loose media bioreactor 802. An output sludge 815 can be formed and dosed into the AD. In some embodiments, a loose fermentation media such as 812 may be combined in the same reactor with a fixed electroactive media 806. In yet other embodiments, a fixed fermentation media 807 may be combined in the same reactor with a loose electroactive media 813.

Cartridge bioreactor 803 can be composed of a cartridge biocatalyst formation section 816 and a cartridge fermentation section 817. The sludge flow can follow an outside-in pattern such that the fermentation media are contacted first. Cartridge bioreactor 803 can take a sludge feed 820, which can undergo fermentation on cartridge fermentation media 819 located at the outside section of the cartridge toward a sufficient concentration of LMWO, which is suitable for the biocatalyst formation on loose electroactive media 818. The cartridge fermentation media can be amenable to dissimilatory iron reducing bacteria, some of which also possess electro-syntrophic metabolism. An output sludge 821 can be formed and dosed into the AD.

In some embodiments, a designated upstream fermentation vessel is not installed, and fermentation media are not present within the bioreactor column, wherein the fermentation process can be located within existing treatment plant infrastructure, for example by extending the retention times of feed sludge within holding tanks, flow-through vessels, or sludge-thickener units, and allowing pH to drop to around about 3.5 to about 5.0, about 4.0 to about 5.5, or about 5.0 to about 6.5, thereby increasing the content of LMWO in the fermented sludge feed.

Figure 9:
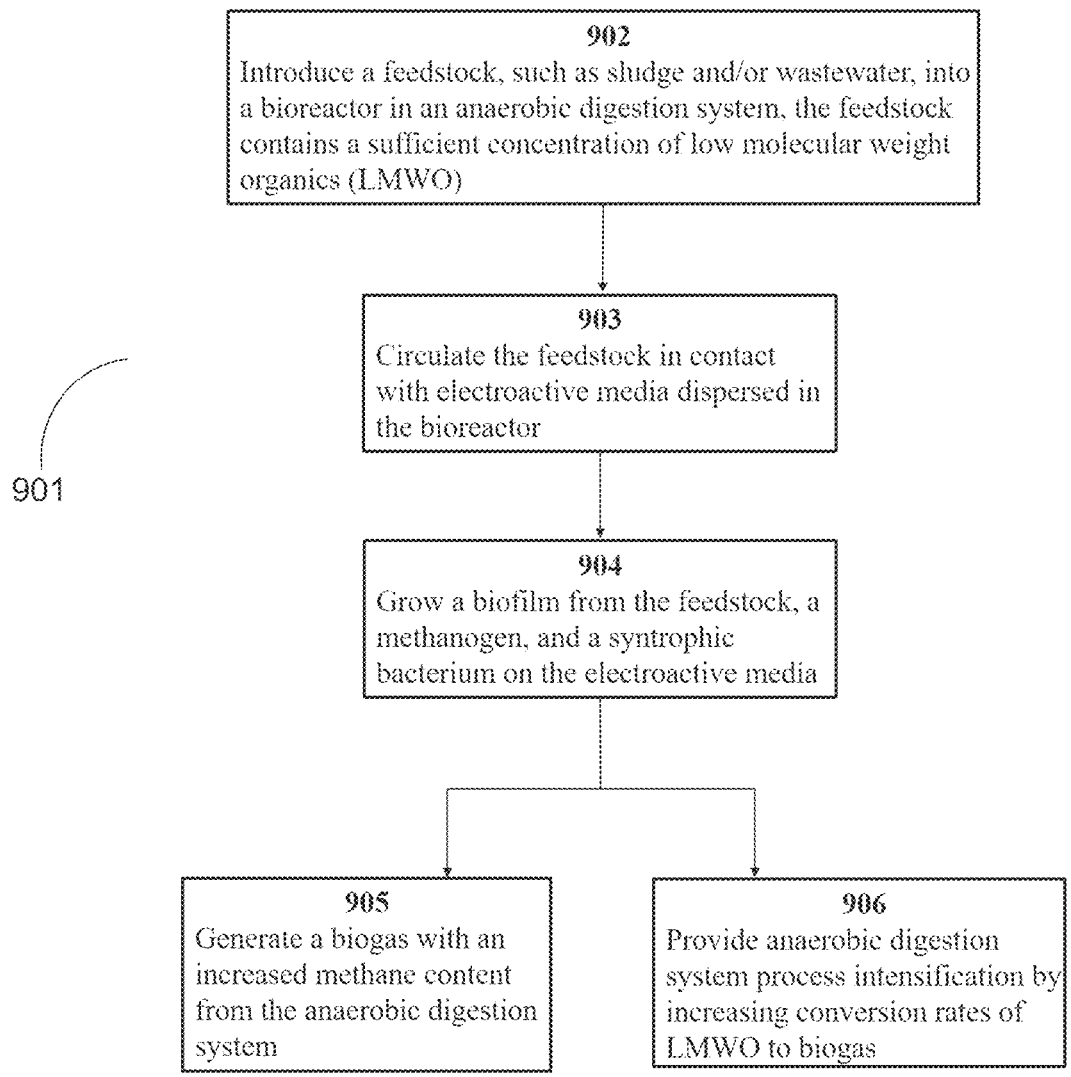
FIG. 9 depicts a flowchart of an anaerobic digestion process, according to some embodiments of the present disclosure.

Referring to FIG. 9, according to some embodiments of the present disclosure, a method 901 of treating wastewater in an anaerobic digestion system. The method can include 902 introducing a feedstock, such as sludge and/or wastewater, into a bioreactor in the anaerobic digestion system and 903 circulating the feedstock in contact with electroactive media dispersed inside the bioreactor. The method can further include 904 growing a biofilm from the feedstock, a methanogen, and a syntrophic bacterium on the electroactive media. A biogas stream can be generated 905 with an increased methane content from the anaerobic digestion system. In addition, the anaerobic digestion system can be intensified 906 due to the increased rate of LMWO conversion to biogas.

The high-rate metabolisms, high microbial density and adsorptive chemistry of the electroactive media, when applied as prescribed by the current disclosure, can improve the performance an anaerobic digestion system at least in four ways: an increase in system methane generation rate; an increase in system biogas methane content; an increase in system COD removal rate (with related side-effects of higher AD loading rates, AD, and/or decreased AD hydraulic retention time); and improved AD stability (i.e. resilience to souring etc). Together, these performance improvements provide a more efficient conversion of waste sludge to bio-energy.

The disclosed bioreactor as retrofit chambers for the state-of-the-art anaerobic digestion system can have the following industrial applicability:

1. a significant biogas methane increase from about 50-60% to above 90%.
2. as retrofit for biomethane production, can ease transition from solids management to renewable energy gas (RNG) production.
3. as retrofit for process intensification, can delay capital projects for WRRF expansion.
4. reduced process footprint in crowded plants where space is at a premium.
5. improved stability, thereby reducing costly downtime associated with process upsets.
6. production of much improved biogas quality for injection to natural gas grid, thereby reducing or eliminating biogas upgrading steps which are a significant cost of biomethane production.
7. improved biogas quality for more efficient combined heat and power cogeneration (CHP)

Presented below are examples discussing the design and evaluation of efficacy of new anaerobic digestion system for treating wastewater. The following examples are provided to further illustrate the embodiments of the present disclosure, but are not intended to limit the scope of the disclosure. While they are typical of those that might be used, other procedures, methodologies, or techniques known to those skilled in the art may alternatively be used.

EXAMPLES

Example 1

Improved Biogas Output Based on the Disclosed Bioreactor

Installations of the SEED process involve a bank of multiple bioreactors, with a total volume between about 1 and 25% of the AD volume. The following example presents non-limiting design, operation, and evaluation criteria for a continuously-fed fixed media bioreactor treating a thickened and fermented primary sludge with about 4% solids content. For a total bioreactor bank volume which is about 1% of a 5300 m$^3$ AD, about 3 to 7 bioreactors can provide the necessary volume while also providing operational redundancy for shutdown and maintenance of the reactors (e.g. electroactive media replacement). A bioreactor height to diameter ratio of about 2 and internal sludge velocity of about 2 m/h can be used. Total flow through the bioreactor bank can depend on configuration of the anaerobic digestion system, strength of feed substrate and size of the reactors, ranging from about 1-100% of AD flow. Substrate concentration of the fermented feed sludge can be between about 5 and 80 Kg(COD)/m$^3$, with typical values falling within a range of about 40 to 60 Kg(COD)/m$^3$. Dilution of sludge via recirculation is used to lower bioreactor inlet feed strength to between about 1 and 10 Kg(COD)/m$^3$ while still providing requisite velocity. Volumetric organic loading rates depend on the biodegradability of the sludge and the total mass of active microorganisms within the reactor, otherwise known as the food to microorganism ratio (F/M) or substrate to inoculum ratio (SIR). The volumetric organic loading rate is the application of soluble and particulate organic matter to the bioreactor expressed as kilograms of chemical oxygen demand per cubic meter. A target F/M ratio to assist with choosing a reactor loading rate can be between about 1 and 6 kilograms biodegradable COD per kilogram active VSS per day (i.e. 1-6 Kg(bCOD)/Kg(VSSa)·d), which can enable volumetric organic loading rates between about 2 and 30 kilograms COD per cubic meter bioreactor volume per day (i.e. about 2-30 Kg(COD)/m$^3$·d), depending on reactor active biomass density. Fixed electroactive media specific surface area is between about 25 and 250 m$^2$/m$^3$ (units being square meters of media geometric surface area per cubic meter reactor working volume). Fixed media of lower specific surface area (about 50 m$^2$/m$^3$) are used for sludges prone to extreme media fouling, whereas fixed media with higher specific surface areas (about 150 m$^2$/m$^3$) and consequentially less void volume are typically used for sludges with low to moderate fouling potential, which can be evaluated using bench-scale experimentation. Backwash flow rates for fixed media bioreactors typically involve increasing inlet sludge flow by about 2 to 10-fold, making use of recirculation loop pumps to avoid organic over-loading. Backwash biogas surface loading rates range from about 2 to 20 liters of biogas per minute-square meter (about 2-20 L/min·m$^2$). Ultimately, backwash protocols can depend on media type, sludge behavior and media fouling rate.

Measures used to evaluate process efficacy include COD removal efficiency follow Equation 1 below.

$$\frac{sCOD_{in} - sCOD_{out}}{sCOD_{in}} * 100\% \qquad \text{Equation 1}$$

Where $sCOD_{in}$ denotes the soluble COD concentration of bioreactor feed sludge (M·L$^{-3}$), and $sCOD_{out}$ denotes bioreactor effluent sludge soluble COD (M·L$^{-3}$). Routine operation of fixed media reactors incurring F/M ratios of about 1.5 typically achieve greater than about 90% removal efficiency of soluble COD. Removal efficiencies for sCOD which fall below this threshold indicate organic overloading or an overly aggressive backwash regime. Methane conversion efficiency (MCE, Equation 2 below below) is another measure of process performance, and for the above operation and media type the MCE values are typically in the range of about 70-90%.

$$\frac{COD_{methane}}{TCOD_{in} - TCOD_{out}} * 100\% \qquad \text{Equation 2}$$

Where $COD_{methane}$ denotes the daily mass of methane-as-COD produced ($M \cdot T^{-1}$), while $TCOD_{in}$ and $TCOD_{out}$ ($M \cdot T^{-1}$) denote daily mass of total COD present in reactor influent and effluent, respectively. High MCE values indicate proper upstream fermentation, efficient conversion of LMWO and an enriched methanogen community within the anaerobic digestion system. Methane content in produced biogas is another important metric of process performance, indicating both the production of methane and removal of carbon dioxide. Biogas methane content, like the previous two performance indices, is presented as a percentile and can range from about 50-60% to greater than 95%. High biogas methane content (about 80-95%) indicates enriched methanogen communities, autotrophic metabolisms, and efficient adsorptive and absorptive processes within the anaerobic digestion system. Specific methane production rate (SMPR) is yet another process performance criterion, and is calculated by dividing the daily volume of methane produced by the reactor sludge volume, and has units of $L_{CH4}/L_{reactor} \cdot d$, and can range from between about 0.3 and 3.5 $L_{CH4}/L_{reactor} \cdot d$. A high SMPR (greater or equal to 1 $L_{CH4}/L_{reactor} \cdot d$) indicates proper upstream fermentation, rapid conversion of LMWO, and an enriched methanogen community within the anaerobic digestion system.

The SEED process was evaluated in a biokinetic model to compare the performance of an unamended 5400 m³ anaerobic digester (AD) to that of one augmented daily with SEED biocatalyst. A bank of SEED bioreactors was investigated at several different size scales. Each size scale was modelled separately to determine the effect of sizing on system performance. Four different volumetric scales (1%, 2%, 5%, 10%) relative to AD were investigated, where each size scale contained five SEED bioreactors. The five SEED bioreactors within the bank not only allowed for four days of media-biofilm regrowth between media harvesting events, wherein several methanogen doubling events could occur, but also a bioreactor suspended growth time-frame similar to the AD minimum sludge retention time (SRT), facilitating suspended biomass adaptation between vessels. The bioreactors were simulated to be fed with fermented primary sludge of 53 Kg(COD)/m³ concentration. Fermented feed contained 25% biodegradable soluble COD (bsCOD), with the remainder being particulate COD containing a 30% non-biodegradable component. The optimal organic loading rate (OLR) for global process (SEED reactors plus enhanced AD) methane output at each volumetric scale was identified and the results presented in FIG. 10. Optimal methane output is a function of both methanogen activity (methane output per cell) and abundance. Methanogen activity and abundance in turn are contingent upon the organic loading rate, which plays a role in shaping bioreactor biofilm methanogen concentrations and substrate fluxes for LMWO conversion to methane. Model results showed that a SEED bioreactor OLR of 14 Kg(COD)/m³·d provided ample substrate without exceeding biomass metabolic capacity, the upper limit of which was described by a maximum food to mass ratio of 1.5 Kg(bsCOD)/Kg(VSSa)·d. At this loading, the 1% SEED scaling provided an 11% increase in global system methane output when active SEED biocatalyst was dosed daily to the downstream AD; 2% scaling provided a 23% increase in methane output; 5% scaling provided a 57% increase in methane output; while 10% SEED scaling relative to main AD provided upwards of 99% increases in global system methane output. SEED food to mass ratios of between 1 and 1.5 Kg(bsCOD)/Kg(VSSa)·d for the indicated scales provided safe loading rates for ideal biocatalyst formation.

The main AD feed flow set-point was about 193 m³/d. Fermented TSPS feed flow rates entering a single SEED bioreactor ranged from about 1% to 10% of the main AD flow for the four scales, respectively. A fixed media element with specific surface area of about 150 m⁻¹ provided electroactive area for the fixed biofilm to remove an average of about 94% of bCOD in SEED influent by way of biofilm substrate fluxes ranging from about 2 to 4.6 mg/cm²·d in all scales evaluated. Internal hydrolytic rates for primary sludge were accounted for. Specific methane production rate within the SEED reactors was about 2.06 $LCH_4/L_{reactor} \cdot d$. High biocatalyst methanogen densities in the variously scaled SEED systems enriched downstream AD active VSS from 943 mg/L to upwards of 1566 mg/L, constituting a 66% increase and extending the effective sludge retention time of the AD and decoupling it from the AD hydraulic retention time. Steady-state increases in methanogenic abundances took longer (up to nearly one year) for smaller SEED scales.

Figure 10:
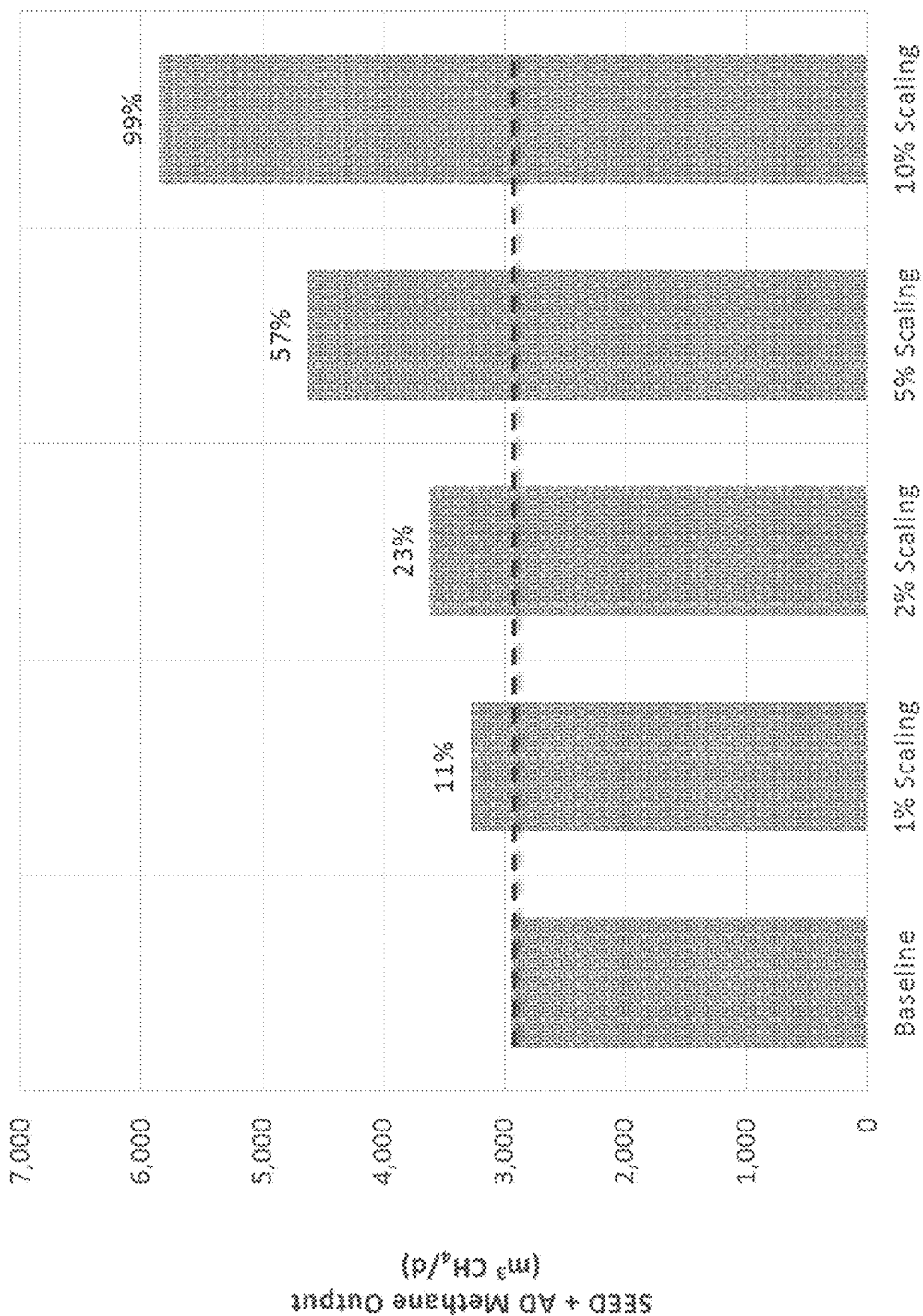
FIG. 10 depicts the methane output improvement based on a fixed media bioreactor, according to some embodiments of the present disclosure.

Media backwash and biocatalyst dose frequency was fixed on a four day cycle, corresponding to multiple high-rate methanogen doubling events. Operationally, one of the five bioreactors would dose biocatalyst into the digester, followed by a four day ripening period while the other reactors took turns dosing in succession. The SEED process lessens methanogen requirements for constitutive cell maintenance, liberating metabolic energy for cell synthesis. This results in greater cell densities for bioaugmentation. As shown in FIG. 10, the additional steady state methane production rate for the global system ranged between 337 and 2912 m³ $CH_4$/d, with a greater proportion of methane having been generated within the enhanced AD rather than the SEED reactors themselves. A key component of the SEED process is the ability to ensure dosed biocatalyst retains its activity in the receiving environment. In some cases this requires increases in the digester loading rate so that bulk sbCOD concentrations remain above the minimum for positive biocatalyst net specific growth rate. In the current example, the potential for even greater methane production due to a SEED process retrofit exists if the dose rate is increased from a four-day to a two-day ripening cycle, which is amenable for optimized bioreactor feed types containing trace metals, nutrients, and sufficient quantities of desirable LMWO such as ethanol and acetate.

In summary, modeling efforts demonstrate the potential of the SEED process to increase global system methane output from 11% to 99% with the addition of SEED bioreactors $\frac{1}{100}^{th}$ to $\frac{1}{10}^{th}$ the size of a full-scale AD. Modeling efforts represent preliminary insights into SEED process performance and remain subject to refinement as empirical kinetic and activity values are elucidated through bench and pilot-testing.

Example 2

Enhanced Microbial Activity and Diversity Using the Disclosed Bioreactor

Microbial species can have a temporal shift in relative abundance and community composition within a bioreactor. An accelerated change in microbial activity in the community, facilitated by effective colonization of loose electroactive media by archaea and syntrophic bacteria, can lead to an enhanced rate of biomethane production within the first five to ten days of the reaction process.

Laboratory-scale testing was conducted and evaluation criteria were examined for a bioreactor utilizing loose media to treat a thickened and fermented primary sludge under both mesophilic and thermophilic anaerobic digestion conditions. A batch-fed bioreactor system was simulated by small-scale biochemical methane potential (BMP) assays. The batch-fed char amended bioreactors and control bioreactors were incubated in temperature controlled shakers at about 38 and 55° C. to simulate mesophilic and thermophilic anaerobic digestion, until they stopped producing methane, which was typically about 50 to 80 days. Each process configuration was assessed in triplicates. Further details of the procedure for testing can be found in Cimon et al., (2020) *Bioresour. Technol.* 297:122440, which is incorporated by reference in its entirety.

Figure 11A:
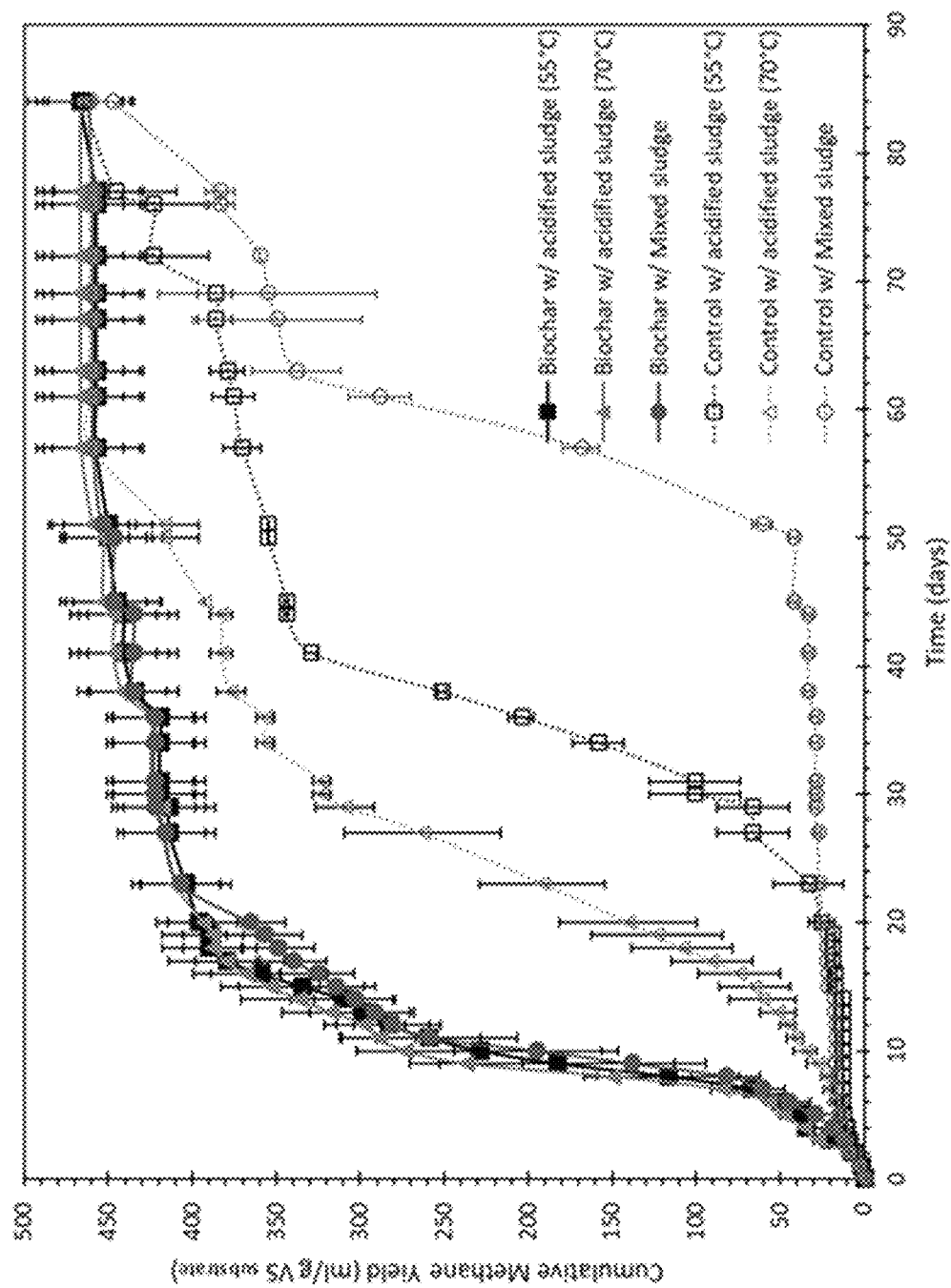
FIG. 11A illustrates temporal progression of specific cumulative methane yield from bioreactors utilizing inocula and three different substrates, including acidified sludge at about 55° C., acidified sludge at about 70° C., and mixed sludge, according to some embodiments of the present disclosure.
Figure 11B:
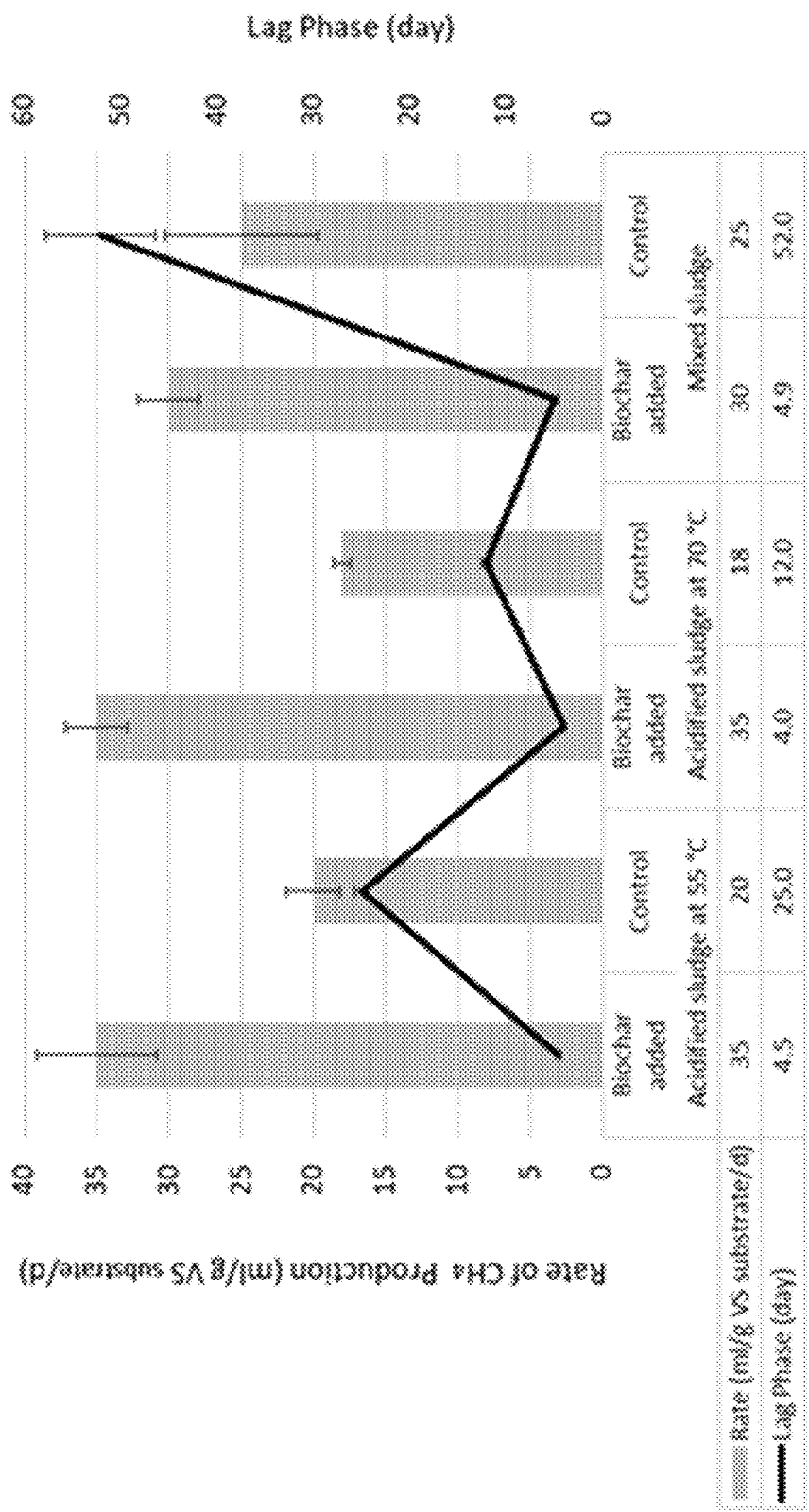
FIG. 11B illustrates temporal progression of kinetic constants including rate of specific methane production and lag phase, according to some embodiments of the present disclosure.

Acidification of thickened and fermented primary sludge substrate was examined during the acid phase of a temperature phased anaerobic digestion system, as shown in FIGS. 11A and 11B. Acidification of sludge was intended to promote direct interspecies electron transfer for the bioreactor system enhanced by loose media. Acidification assists bacteria, with electron conducting pilin, to degrade complex organic molecules. Certain species of bacteria can have a limited capacity to degrade complex organic molecules Zhao et al., (2017) *Water Res.* 115:266-77.

Microbial colonization and methane production efficacy based on loose electroactive media were assessed by percent acceleration in the methane production rate. Improvements on anaerobic digestion processes were also examined by percent reduction in lag phase duration along with temporal changes in microbial relative abundance and diversity in a bioreactor. Lag phase is defined as the period of time between the introduction of a microbial culture into a bioreactor and time whereby the generation of methane begins.

Testing results were compared to experimental design controls, i.e. anaerobic digestion with no loose media. Under both mesophilic and thermophilic conditions, addition of loose media enhanced the rate of methane production considerably, while the lag phase for methane generation was substantially shortened. The following results from FIGS. 11A and 11B show efficiencies produced by the addition of loose media relative to control replicates within a thermophilic bioreactor. FIG. 11A illustrates the temporal progression of specific cumulative methane yield from bioreactors utilizing inocula and three different substrates, including acidified sludge at about 55° C., acidified sludge at about 70° C., and mixed sludge composed of a mixture of primary and secondary sludge. Solid lines in FIG. 11A represent bioreactors amended with biochar and dashed lines indicate control samples without biochar. All bioreactors had a substrate to inoculum ratio (SIR) of 4.4 g-volatile solids (VS)/g-VS. FIG. 11B illustrates the temporal progression of kinetic constants (rate of specific methane production and lag phase) of Modified Gompertz Model. Data are means of triplicates, and error bars show standard deviations. The data in FIGS. 11A and 11B indicate biochar enhances the specific methane generation rates up to 93% in the first 10 days and shortens initial lag phase (to exponential methane generation) up to 961%, compared to control samples without biochar. The application of loose media, utilizing acidized sludge, yielded specific methane rates of approximately 35 mL $CH_4$/g-VSsubstrate/d, controls yielded lower daily methane production at about 18-25 mL $CH_4$/g-VSsubstrate/d. Compared to controls, the use of loose electroactive media enhanced methane generation by about 93%. Control bioreactors absent of the electroactive media experienced acute inhibition with lag phases ranging from about 12-52 days, while those which utilized the loose media began generating methane from about day 4, as shown in FIG. 11b. The present example shows that by utilizing loose media, lag time can be considerably reduced, leading to a decrease in required sludge retention time during the anaerobic digestion process.

Figure 13:
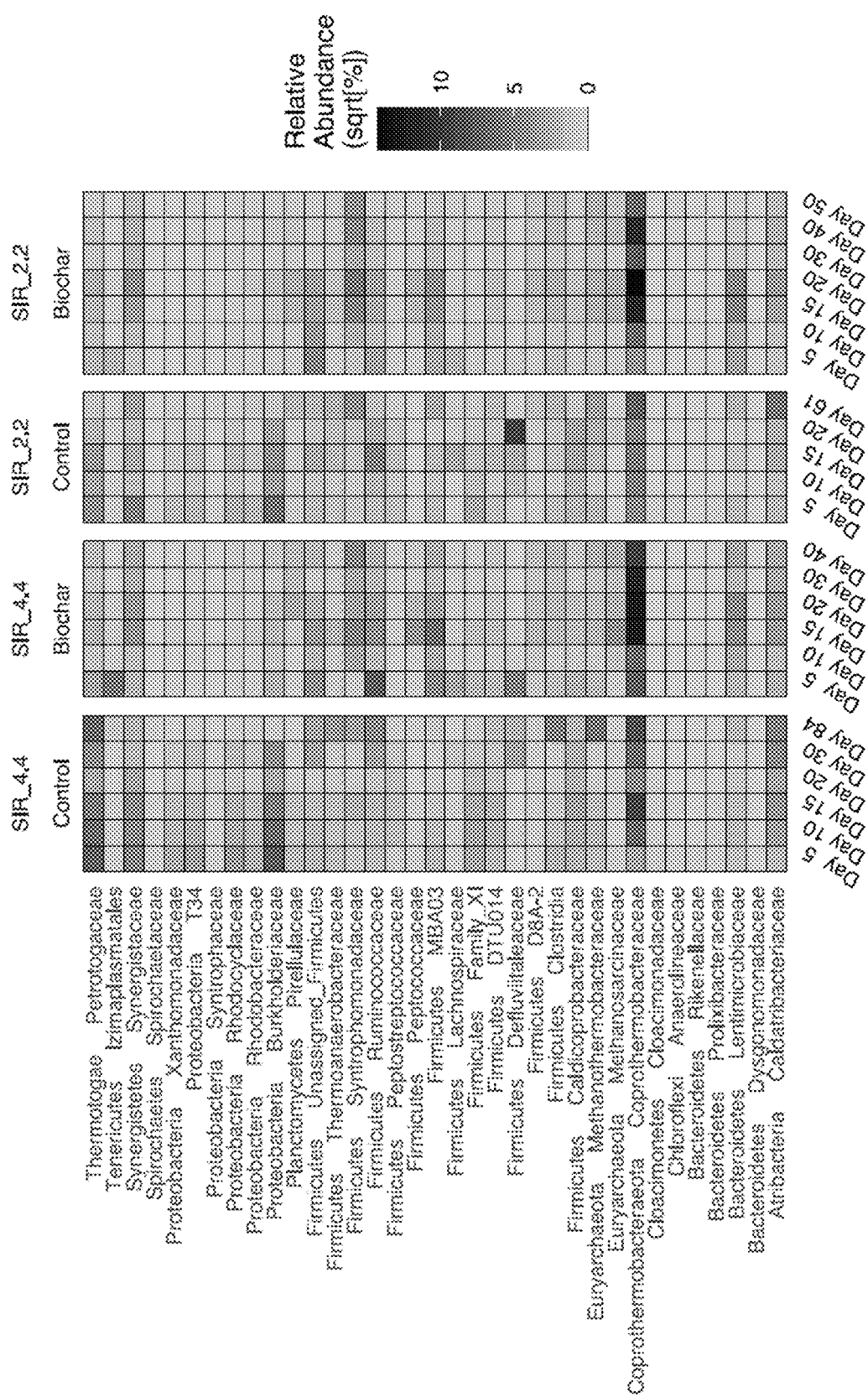
FIG. 13 is a heatmap showing the relative abundances (% of total community) of the most highly represented populations during anaerobic digestion, according to some embodiments of the present disclosure.

DNA fingerprinting targeting the V4-5 regions of the small subunit ribosomal RNA (SSU or 16S rRNA) gene identified 186 microbial families associated with loose media amended samples. When compared to control samples, those containing loose media realized considerable microbial community enrichment. The enriched community included 45 families representing 11 bacterial phyla including: Coprothermobacteraeota, Firmicutes, Atribacteria, Bacteroidetes, Synergistetes, Tenericutes, Planctomycetes, Armatimonadetes, Chloroflexi, Actinobacteria, and Gemmatimonadetes and 1 archaeal phylum Euryarchaeota (containing all known methanogens). Nine of the enriched phyla encompassing the families Coprothermobacteraceae, Unassigned_Firmicutes, Caldatribacteriaceae, Syntrophomonadaceae, Methanothermobacteraceae, Lentimicrobiaceae, Synergistaceae, MBA03, Ruminococcaceae, Defluviitaleaceae were considered dominant community members (representing >1% of total community per phyla). The majority of these families are implicated in late stages of fermentation and syntrophy. Methanogenic enrichment in the loose media amended samples was dominated by Methanothermobacteraceae with additional enrichment of Methanosarcinaceae and Methanomassiliicoccaceae. Genomic research results indicate specific microbial families are associated with successive stages of methane production from organic matter inputs exposed to loose electroactive media, as shown in FIG. 13.

Figure 12:
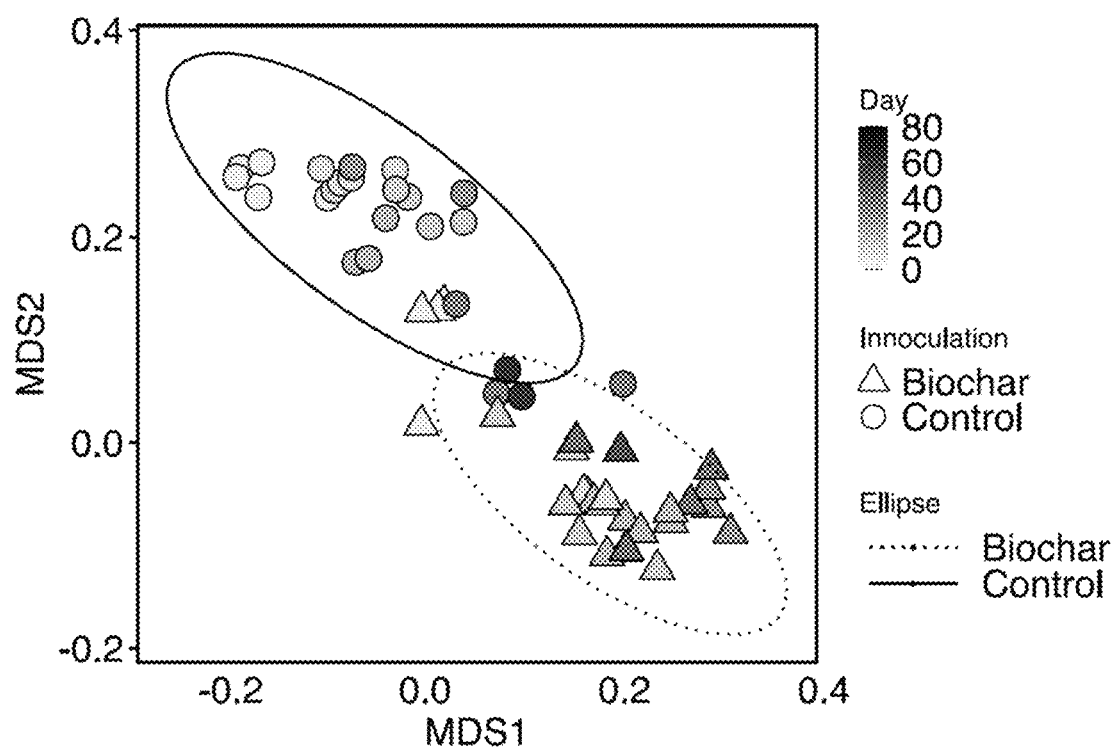
FIG. 12 illustrates non-metric multidimensional scaling plot showing relationships between inoculation type (control and biochar) over time (filled points), according to some embodiments of the present disclosure.

In addition, temporal changes in microbial community structure were observed during time course experiments within loose media amended samples. Non-metric multidimensional scaling of DNA fingerprint patterns revealed a succession of bacterial and archaeal groups associated with enhanced methane production in the loose media amended samples (FIG. 13). In the loose media amended assays there was a more rapid succession to a stable methanogenic community structure when compared to controls which had a slower successional process and different community structure (FIGS. 12 and 13). The temporal successional shift is reflected in the methane production rate, where loose media amended samples yielded a higher slope in methane production during beginning and middle stages of bioreactor operation. The process can be subdivided into early, middle and late stages in which conditions favoring methanogenic consortium formation are selected. These conditions are further differentiated on the basis of comparing sieved loose media to total microbial diversity to identify microorganisms that are specifically attached to finer textured surfaces. Proteobacteria, Firmicutes and Coprothermobacteraeota phyla including the families Syntrophomonadaceae, Ruminococcaceae, Peptococcaceae, Syntrophaceae, and Coprothermobacteraceae, and methanogenic Methanosarcinaceae were all enriched on finer textured loose media surfaces.

Those skilled in the art will recognize, or be able to ascertain, using no more than routine experimentation, numerous equivalents to the specific composition and procedures described herein. Such equivalents are considered to be within the scope of this disclosure, and are covered by the following claims.

What is claimed is:

1. A bioreactor in an anaerobic digestion system for treating wastewater, the bioreactor comprising:
an enclosed cylinder comprising:
a central draft tube;
a main annular space surrounding the central draft tube;
an electroactive medium in a fixed configuration dispersed within the enclosed cylinder;
an inlet for introducing a feedstock into the enclosed cylinder in contact with the electroactive medium; and
an outlet for outputting the feedstock after treatment.

2. The bioreactor of claim 1, wherein the electroactive medium comprises a basal cloth support sandwiched by two layers of carbon cloth.

3. The bioreactor of claim 2, wherein a steel, polyethylene or polycarbonate screen is placed on the carbon cloth to provide a turbulent flow for an enhanced mass transfer and longevity.

4. The bioreactor of claim 2, wherein a conductive nanomaterial is bonded onto the carbon cloth.

5. The bioreactor of claim 1, wherein the electroactive medium is configured into a pleated arrangement, a lobate arrangement, a honeycomb arrangement, a flat pack cartridge, or a spiral wrap arrangement.

6. The bioreactor of claim 5, wherein a filter device comprising the electroactive medium is placed in the main annular space.

7. A bioreactor in an anaerobic digestion system for treating wastewater, the bioreactor comprising:
an enclosed cylinder comprising:
a central draft tube;
a main annular space surrounding the central draft tube;
a loose electroactive medium dispersed within the enclosed cylinder and contained within a porous receptacle,
an inlet for introducing a feedstock into the enclosed cylinder in contact with the electroactive medium; and
an outlet for outputting the feedstock after treatment.

8. The bioreactor of claim 7, wherein the loose electroactive medium is dispersed throughout the central draft tube and the main annular space.

9. A bioreactor in an anaerobic digestion system for treating wastewater, the bioreactor comprising:
an enclosed cylinder comprising:
a central draft tube;
a main annular space surrounding the central draft tube;
a loose electroactive medium dispersed within the enclosed cylinder;
a replaceable container to contain the loose electroactive medium in a second annular space defined by the central draft tube and the replaceable container;
an inlet for introducing a feedstock into the enclosed cylinder in contact with the electroactive medium; and
an outlet for outputting the feedstock after treatment.

10. The bioreactor of claim 9, wherein the replaceable container comprises an outer barrier wrap to allow the feedstock to flow between the main annular space and the second annular space but contain the loose electroactive medium inside the replaceable container.

11. An anaerobic digestion system for treating wastewater, the system comprising the bioreactor according to claim 1, 7 or 9 and a main anaerobic digester placed downstream of the bioreactor.

12. The anaerobic digestion system of claim 11, comprising a fermentation section placed upstream of the bioreactor.

13. The anaerobic digestion system of claim 12, wherein the fermentation section and the bioreactor are integrated into one reactor vessel.

14. The anaerobic digestion system of claim 11, wherein the electroactive medium is loose and magnetic.

15. The anaerobic digestion system of claim 14, wherein a recycler is used downstream of the bioreactor and/or the main anaerobic digester to collect the magnetic loose electroactive medium.

16. The recycler of claim 15, wherein an electromagnet is used to gather the magnetic loose electroactive medium from a bioreactor and/or a main anaerobic digester discharge.

17. The bioreactor of claim 1, 7, or 9, wherein the electroactive medium is natural or man-made.

18. The bioreactor of claim 7 or 9, wherein the loose electroactive medium is selected from biochar, activated carbon, wood ash, and magnetic mineral.

19. The bioreactor of claim 1, 7, or 9, wherein the feedstock is sludge or wastewater.

20. A method of treating wastewater in an anaerobic digestion system, the method comprising:
introducing a feedstock comprising a sufficient concentration of organics derived from the wastewater into a bioreactor;
circulating the feedstock in contact with an electroactive medium dispersed inside the bioreactor;
growing a biofilm from the feedstock, a methanogen, and a syntrophic bacterium on the electroactive medium;
converting the organics into a biogas within the anaerobic digestion system;
back injecting a fraction of the biogas or an externally-generated hydrogen into the bioreactor for mixing, purification, or amelioration of methane production;
scouring the biofilm from the electroactive medium by a liquid shear force of the feedstock, and/or biogas injection; and
dosing a biocatalyst comprising the biofilm and/or an electron-conductive supplement into a main anaerobic digester downstream of the bioreactor,
thereby increasing a methane content in the biogas and increasing digestion system capacity.

21. The method of claim 20, comprising collecting the biogas from the bioreactor and/or the main anaerobic digester.

22. The method of claim 20, wherein the electroactive medium comprises a loose electroactive medium.

* * * * *